US008075494B2

(12) United States Patent
Margolis et al.

(10) Patent No.: US 8,075,494 B2
(45) Date of Patent: Dec. 13, 2011

(54) AUDIOGRAM CLASSIFICATION SYSTEM

(75) Inventors: Robert H. Margolis, Arden Hills, MN (US); George L. Saly, Edina, MN (US)

(73) Assignee: Audiology Incorporated, Arden Hills, MN (US)

( * ) Notice: Subject to any disclaimer, the term of this patent is extended or adjusted under 35 U.S.C. 154(b) by 624 days.

(21) Appl. No.: 11/681,979

(22) Filed: Mar. 5, 2007

(65) Prior Publication Data

US 2008/0221719 A1 Sep. 11, 2008

(51) Int. Cl.
*A61B 5/00* (2006.01)
(52) U.S. Cl. .......................................... 600/559; 381/60
(58) Field of Classification Search ................. 600/559; 381/60
See application file for complete search history.

(56) References Cited

U.S. PATENT DOCUMENTS

2004/0008849 A1 1/2004 Moller
2004/0073134 A1 4/2004 Wasden et al.
2006/0074572 A1 4/2006 Bye et al.

OTHER PUBLICATIONS

Carter, Howard A., Tentative Standard Procedure for Evaluating the Percentage of Useful Hearing Loss in Medicolegal Cases, Jour. A.M.A., Aug. 1, 1942, pp. 1108-1109.
Mangham, Charles A., Hearing threshold difference between ears and risk of acoustic tumor, Otolarngology—Head and Neck Surgery, vol. 105 No. 6, Dec. 1991, pp. 814-817, Seattle, Washington.
Paparella, Michael M. et al, Meniere's Disease and the Peak Audiogram, Arch Otolaryngol, vol. 108, Sep. 1982, pp. 555-559.
Clark, John Greer, Uses and abuses of hearing loss classification, Asha-0001-2475/81/230-493-08, Jul. 1981, American Speech-Language-Hearing Association.
Pittman, A.L. et al., Hearing Loss in Children and Adults: Audiometric Configuration, Asymmetry, and Progression, Jun. 2003, pp. 198-205, Ear & Hearing, vol. 24, No. 3, Lippincott Williams & Wilkins, U.S.A.
Roeser et al, Degree of Hearing Loss, 2000, Chapter 11, Applications in Diagnostic Audiology.
Cheng-Shun Lee, et al., Audiological Profiles and Menier's Disease, ENT—Ear Nose & Throat Journal, Aug. 1995, pp. 527-532, vol. 74, No. 8, MEDQUEST Communications, Inc., Minneapolis, Minnesota.
Guild, Stacy R., The Laryngoscope. A Method of Classifying Audiograms, Otological Research Laboratory, John Hopkins University, Nov. 8, 1932, pp. 821-836.
Keith, RW., The Audiologic Evaluation in Northern JL Hearing Disorders, 3rd Edition, 1996, Ch. 4, p. 50 of pp. 45-56, Allyn & Bacon, Boston.
Bess, FH, et al., Audiology: The Fundamentals, 1990, p. 78, Williams & Wilkins, Baltimore.
Carhart, Raymond, An Improved Method for Classifying Audiograms, Laryngoscope 55:640-662, 1945, Butler, Pennsylvania.
Fowler, E.P., et al., Audiometric Methods and Their Applications, Trans of the Amer Laryngological, Phinological, and Otological Soc. 1922, pp. 98-132.
Stach, Brad A., Clinical Audiology: An Introduction, 1998, pp. 105-108, singular Publ. Group, San Diego.
Tempest, W., Medico-Legal Aspects of Noise-Induced Hearing Loss, S.D.G. Stephens (ed.), Disorders of Auditory Function, 1976, pp. 87-96, Academic Press, London.

(Continued)

*Primary Examiner* — Max Hindenburg
*Assistant Examiner* — Renee Danega
(74) *Attorney, Agent, or Firm* — Fredrikson & Byron, P.A.

(57) ABSTRACT

An audiogram classification system is provided. The classification system includes categories for configuration, severity, site of lesion and/or symmetry of an audiogram. A set of rules can be provided for selecting the categories, wherein the set of rules ignore one or more local irregularities on an audiogram and have been validated to maximize agreement with judges.

35 Claims, 15 Drawing Sheets

OTHER PUBLICATIONS

Macrae, J.H., A Procedure for Classifying Degree of Hearing Loss, Journal of the Oto-Laryngological Society of Australia, 1975-76, pp. 26-35, vol. 4, No. 1.

Cohen, Jacob, A Coefficient of Agreement for Nominal Scales, Educational and Psychological Measurement, 1960, pp. 37-46, vol. XX, No. 1.

Davis, Hallowell, Guide for the Classification and Evaluation of Hearing Handicap in Relation to the International Audiometric Zero, American Academy of Ophthalmology and Otolaryngology, 1965, pp. 740-750.

Fletcher, Harvey, Speech and Hearing, Bell Telephone Laboratories, Inc., 1929, pp. 198-201, D. Van Nostrand Company, Inc., New York.

Kaplan, Harriet, et al., Educational and Communicative Implications of Hearing Loss, Audiometric Interpretation: A Manual of Basic Audiometry, pp. 11-14 and 315-319, 2nd Edition, Allyn & Bacon, Boston, 1993.

Martin, Frederick N., Introduction to Audiology, 1986, p. 75, Prentice-Hall, Inc., 3rd Edition, New Jersey.

Neary, W.J., et al., A clinical, genetic and audiological study of patients and families with unilateral vestibular schwannomas. II. Audiological findings in 93 patients with unilateral vestibular schwannomas, The Journal of Laryngology and Otology, Dec. 1996, pp. 1120-1128, vol. 110, Manchester, UK.

Savastano, Marina, et al., Evolution of Audiometric Pattern in Meniere's Disease: Long-Term Survey of 380 Cases Evaluated According to the 1995 Guidelines of the American Association of Otolaryngology-Head and Neck Surgery, The Journal of Otolaryngology, Nov. 6, 2005, pp. 1-5, vol. 34.

Yantis, Phillip A., Puretone Air-Conduction Threshold Testing, In Katz, J. (ed.) Handbook of Clinical Audiology, 4th edition, 1994, pp. 97-108, Williams & Wilkins, Baltimore.

Figure 3

AUDIOGRAM CLASSIFICATION SYSTEM

| Configuration | Severity | Site of Lesion | Symmetry |
|---|---|---|---|
| Normal Hearing | | Conductive | Symmetrical Hearing Loss |
| Flat Hearing Loss | Mild<br>Moderate<br>Severe<br>Profound | Sensorineural<br>Mixed<br>Sensorineural or Mixed | Asymmetrical Hearing Loss |
| Sloping Hearing Loss | Normal-Mild<br>Normal-Moderate<br>Normal-Severe<br>Mild-Moderate<br>Mild-Severe<br>Moderate-Severe<br>Severe-Profound | | |
| Rising Hearing Loss | Mild-Normal<br>Moderate-Normal<br>Moderate-Mild<br>Severe-Normal<br>Severe-Mild<br>Severe-Moderate<br>Profound-Severe<br>Profound | | |
| Trough-shaped Hearing Loss | Mild<br>Moderate<br>Severe | | |
| Peaked Hearing Loss | Mild<br>Moderate<br>Severe | | |
| Other | Mild<br>Moderate<br>Severe | | |

Figure 4

| Variable | Description |
|---|---|
| A | Mean of thresholds T250, T500 |
| B | Mean of thresholds T250, T500, T750, T1000 |
| C | Mean of thresholds T500, T750, T1000, T1500, and T2000 |
| D | Mean of thresholds T1000, T1500, T2000, T3000, and T4000 |
| E | Mean of thresholds T2000, T3000, T4000, T6000, and T8000 |
| F | Mean of thresholds T4000, T6000, and T8000 |
| G | Mean of thresholds T600 and T8000 |
| H | A or B or C |
| I | E or F or G |
| J | Maximum of thresholds T4000, T6000, or T8000 including NR levels |
| K | Maximum of A, B, C, D, or E + Minimum of A, B, C, D, or E |
| MAMin | Minimum of A, B, C, D, E or F |
| MAMax | Maximum of A, B, C, D, E or F |
| L | (A-MAMin) + (B-MAMin) + (G-MAMin) |
| Av | Mean of thresholds T500, T750, T1000, T1500, T2000, T3000 and T4000 |
| AV1 | Mean of A, B, C, D, E, F and G |
| Tmax | Maximum of thresholds T500, T750, T1000, T2000, T3000, or T4000 |
| Tmin | Minimum of thresholds T500, T750, T1000, T2000, T3000, or T4000 |

Figure 5

| Configuration | Severity | Not | Air Conduction Moving Average (MA) | | | | | | | |
|---|---|---|---|---|---|---|---|---|---|---|
| | | | A 250-500 | B 250-1000 | C 500-2000 | D 1000-4000 | E 2000-8000 | F 4000-8000 | G 600-8000 | Av 500-4000 |
| Normal Hearing | | | Av <= 20 AND B <= 20 AND E <= 25 AND MaMax < 23 | | | | | | | 500-4000 |
| Flat Hearing Loss | Mild | Normal | [K<=15 OR \|A-F\|<=15] AND MAmax - F <15; AND C-F>-30; AND Tmax-Tmin <25 (500-4000); {if MAmax - A > 7.4 AND MAmax - F > 7.4 not flat}; {if A - MAMin > 7.4 AND G - MAmin > 10 AND L > 33, not flat}; If A>=20 AND B<20 AND C<20 AND D<20 AND E>=21 AND F>27, Not Flat; If A>=20 AND B>20 AND D<17.5 AND E<15 AND F<=15, Not Flat | | | | | | | Av < 40 |
| | Moderate | | | | | | | | | 40<=Av<60 |
| | Severe | | | | | | | | | 60<=Av<88 |
| | Profound | | | | | | | | | Av >= 88 |
| Sloping Hearing Loss | Normal-Mild | Normal,Flat, | | B <= 20 | A-F < -17 OR [A<20 AND B<20 AND C<20 AND D>=20 AND E>=21 AND F>27]; If MAMax - A > 7.4 AND [MAMax - F > 7.4 OR MAMax - G > 12], Not Sloping; If A-MAMin > 7.4 AND G-MAMin > 10 AND A-F > -45, Not Sloping | | | | | 20 < F < 40 |
| | Normal-Moderate | Normal, Flat, Sloping Norm-Mild | | B <= 20 | | | | | | 40 <= F < 61 |
| | Normal-Severe | Normal, Flat, Sloping Norm-Mod | | B <= 20 | | | | | | F >= 61 |
| | Mild-Moderate | Normal, Flat, Sloping Mild-Sev | | 20<B<=48 | | | | | | 40 < F < 61 |
| | Mild-Severe | Normal, Flat, Sloping Mild-Mod | | 20<B<=48 | | | | | | F >= 61 |
| | Moderate-Severe | Normal, Flat, Sloping Mild-Severe | | 48<B<=65 | | | | | | F >= 61 |
| | Severe-Profound | Normal, Flat, Sloping Mod-Sev | | 65<B<=90 | | | | | | F >= 90 |
| | Profound | Normal, Flat, Any other sloping | | B >= 90 | | | | | | F > 105 |
| Rising Hearing Loss | Mild-Normal | Normal,Flat, | 25<A<40 | MAMax - F >= 15; OR [A>=20 AND B>20 AND D<17.5 AND E<15 AND F<=15]; [if MAMax - A > 7.4 not rising]; [if A - MAMin > 7.4 and MAMax - F > 7.4 and G - MAMin > 10 not rising] | | | | | | F <= 25 |
| | Moderate-Normal | Normal, Flat, Rising Norm-Mild | 40<=A<=60 | | | | | | | F <= 25 |
| | Moderate-Mild | Normal, Flat, Rising Mod-Norm | 40<=A<=60 | | | | | | | 25 < F < 40 |
| | Severe-Normal | Normal, Flat, Rising Mod-Mild | 60<=A<90 | | | | | | | 25 < F < 40 |
| | Severe-Mild | Normal, Flat, Rising Sev-Norm | 60<=A<90 | | | | | | | 40<=F<60 |
| | Severe-Moderate | Normal, Flat, Rising Sev-Mild | 60<=A<90 | | | | | | | 60<=F<90 |
| | Profound-Severe | Normal, Flat, Rising Sev-Mod | A >= 90 | | | | | | | F >= 90 |
| | Profound | Normal, Flat, Rising Prof-Sev | A >= 90 | | | | | | | F >= 90 |
| Trough-Shaped Hearing Loss | Mild | Normal, Flat, Sloping, Rising | MAMax - A > 7.4 AND [MAMax - F > 7.4 OR MAMax - G > 12] | | | | | | | 20<=MAMax<40 |
| | Moderate | | | | | | | | | 40<=MAMax<60 |
| | Severe | | | | | | | | | MAMax >= 60 |
| Peaked Hearing Loss | Mild | Normal, Flat, Sloping, Rising | A - MAMin > 7.4 AND [MAMax - F > 7.4 OR MAMax - G > 12] | | | | | | | Av < 36 |
| | Moderate | Normal, Flat, Sloping, Rising | | | | | | | | 36<=Av<60 |
| | Severe | Normal, Flat, Sloping, Rising | | | | | | | | Av >= 60 |
| Other | Mild | Any Other Category | A - MAMin > 7.4 AND G - MAMin > 10 AND L > 33 | | | | | | | Av < 40 |
| | Moderate | | | | | | | | | 40<=Av<60 |
| | Severe | | | | | | | | | Av >= 60 |

Figure 6

| Site of Lesion | Bone Conduction Thresholds | | | | | | | Air-Bone Gap | | | |
|---|---|---|---|---|---|---|---|---|---|---|---|
| | $B_5$ 500 | $B_1$ 1000 | $B_2$ 2000 | $B_4$ 4000 | | | | $ABG_5$ 500 | $ABG_1$ 1000 | $ABG_2$ 2000 | $ABG_4$ 4000 |
| Conductive | $B_5 < 25$ | $B_1 < 25$ | $B_2 < 25$ | $B_4 < 25$ | ◇ | | | | | | |
| Not | ALL $B_5, B_1, B_2, B_{54} < 30$ | | | | | A or B | A ◇ | $ABG_5 >= 10$ | $ABG_1 >= 10$ | $ABG_2 >= 10$ | $ABG_4 >= 10$ |
| | | | | | | | B * | $ABG_5 >= 15$ T1,T2,T4<=20 | $ABG_1 >= 15$ T5,T2,T4<=20 | $ABG_2 >= 15$ T5,T1,T4<=20 | $ABG_4 >= 15$ T5,T1,T2<=20 |
| Sensorineural | Normal, Conductive | | | | | C or D | C ◇ | $ABG_5 < 10$ | $ABG_1 < 10$ | $ABG_2 < 10$ | $ABG_4 < 10$ |
| | | | | | | | D * | $ABG_5 <= 15$ | $ABG_1 <= 15$ | $ABG_2 <= 15$ | $ABG_4 <= 15$ |
| Mixed | Normal, Conductive, or Sensorineural | | | | | E or F | D + | $ABG_5 <= 10$ | $ABG_1 <= 10$ | $ABG_2 <= 10$ | $ABG_4 <= 10$ |
| | | | | | | | E + | $ABG_5 >= 10$ $B_5 \neq NR$ | $ABG_1 >= 10$ $B_1 \neq NR$ | $ABG_2 >= 10$ $B_2 \neq NR$ | $ABG_4 >= 10$ $B_4 \neq NR$ |
| | | | | | | | F * | $ABG_5 >= 15$ $B_5 \neq NR$ | $ABG_1 >= 15$ $B_1 \neq NR$ | $ABG_2 >= 15$ $B_2 \neq NR$ | $ABG_4 >= 15$ $B_4 \neq NR$ |
| Sensorineural or Mixed | Normal, Conductive, Sensorineural, or Mixed | | | | | | * | $ABG_5 >= 10$ $B_5 = NR$ | $ABG_1 >= 10$ $B_1 = NR$ | $ABG_2 >= 10$ $B_2 = NR$ | $ABG_4 >= 10$ $B_4 = NR$ |

\* Indicates OR condition

◇ Indicates 3 out of 4 conditions must occur

\+ Indicates 2 out of 4 conditions must occur

ALL Indicates all conditions must occur

Figure 7

| Variable | | Conditions | | | | |
|---|---|---|---|---|---|---|
| | | \|AvLt - AvRt\| > 10, wherein Av is Mean of T500, T750, T1000, T1500, T2000, T3000 and T4000 | | | | |
| A | | | | | | |
| B | * | T250R-T250L>5 | T500R-T500L>5 | T1R-T1L>5 | T2R-T2L>5 | T4R-T4L>5 | T8R-T8L>5 |
| C | * | T250L-T250R>5 | T500L-T500R>5 | T1L-T1R>5 | T2L-T2R>5 | T4L-T4R>5 | T8L-T8R>5 |
| D | + | T250R-T250L>10 | T500R-T500L>10 | T1R-T1L>10 | T2R-T2L>10 | T4R-T4L>10 | T8R-T8L>10 |
| E | + | T250L-T250R>10 | T500L-T500R>10 | T1L-T1R>10 | T2L-T2R>10 | T4L-T4R>10 | T8L-T8R>10 |
| F | ◊ | T250R-T250L>15 | T500R-T500L>15 | T1R-T1L>15 | T2R-T2L>15 | T4R-T4L>15 | T8R-T8L>15 |
| G | ◊ | T250L-T250R>15 | T500L-T500R>15 | T1L-T1R>15 | T2L-T2R>15 | T4L-T4R>15 | T8L-T8R>15 |

\* Indicates 3 out of 6 conditions must occur

+ Indicates 2 out of 6 conditions must occur

◊ Indicates 1 out of 6 conditions must occur

Figure 8

| Confuguration | | | | | |
|---|---|---|---|---|---|
| Judge | 1 | 2 | 3 | 4 | 5 |
| 1 | | 65.4 (0.60) | 58.0 (0.51) | 62.8 (0.57) | 62.8 (0.57) |
| 2 | | | 75.3 (0.71) | 68.4 (0.63) | 78.8 (0.75) |
| 3 | | | | 62.8 (0.57) | 74.5 (0.70) |
| 4 | | | | | 66.7 (0.61) |
| CONSENSUS | 73.2 (0.69) | 92.6 (0.91) | 82.3 (0.79) | 78.4 (0.75) | 89.2 (0.87) |
| ALL | 43.0 (0.43) | | | | |
| MEAN OF PAIRS | 67.6 (0.62) | | | | |
| MEAN CONSENSUS | 83.1 (0.80) | | | | |
| Severity | | | | | |
| Judge | 1 | 2 | 3 | 4 | 5 |
| 1 | | 80.5 (0.76) | 78.8 (0.73) | 84.8 (0.81) | 75.8 (0.70) |
| 2 | | | 83.5 (0.79) | 86.6 (0.83) | 84.4 (0.81) |
| 3 | | | | 82.3 (0.78) | 87.0 (0.84) |
| 4 | | | | | 82.3 (0.78) |
| CONSENSUS | 86.6 (0.83) | 92.2 (0.90) | 87.5 (0.84) | 88.7 (0.86) | 86.2 (0.83) |
| ALL | 61.0 (0.61) | | | | |
| MEAN OF PAIRS | 82.6 (0.78) | | | | |
| MEAN CONSENSUS | 88.2 (0.85) | | | | |
| Site of Lesion | | | | | |
| Judge | 1 | 2 | 3 | 4 | 5 |
| 1 | | 69.7 (0.62) | 60.6 (0.51) | 65.8 (0.57) | 68.0 (0.60) |
| 2 | | | 81.0 (0.76) | 79.7 (0.75) | 87.4 (0.84) |
| 3 | | | | 73.6 (0.67) | 80.1 (0.75) |
| 4 | | | | | 77.9 (0.72) |
| CONSENSUS | 73.2 (0.64) | 94.8 (0.93) | 84.9 (0.80) | 84.4 (0.81) | 93.1 (0.91) |
| ALL | 49.8 (0.33) | | | | |
| MEAN OF PAIRS | 74.4 (0.68) | | | | |
| MEAN CONSENSUS | 86.1 (0.82) | | | | |

Figure 9

| Agreement Pairs | |
|---|---|
| normal | normal |
| mild | mild |
| moderate | moderate |
| severe | severe |
| profound | profound |
| normal-mild | normal |
| normal-mild | mild |
| normal-moderate | normal-moderate |
| normal-moderate | mild |
| normal-severe | normal-severe |
| normal-severe | moderate |
| mild-moderate | mild-moderate |
| mild-moderate | mild |
| mild-moderate | moderate |
| mild-severe | mild-severe |
| mild-severe | moderate |
| moderate-severe | moderate-severe |
| moderate-severe | moderate |
| moderate-severe | severe |
| severe-profound | severe-profound |
| severe-profound | severe |
| severe-profound | profound |
| profound | profound |

Figure 10

| AGREEMENT BETWEEN JUDGES AND AMCLASS | | | | | | | |
|---|---|---|---|---|---|---|---|
| Judge | 1 | 2 | 3 | 4 | 5 | Mean | Consensus |
| Configuration | 66.7 (0.61) | 78.4 (0.75) | 73.2 (0.69) | 78.4 (0.75) | 80.1 (0.77) | 62.2 (0.56) | 89.6 (0.88) |
| Severity | 85.7 (0.83) | 86.6 (0.84) | 86.1 (0.84) | 87.4 (0.85) | 81.4 (0.78) | 78.6 (0.75) | 92.2 (0.91) |
| Site of Lesion | 65.4 (0.60) | 81.0 (0.78) | 73.2 (0.69) | 86.6 (0.84) | 80.1 (0.77) | 68.4 (0.63) | 84.8 (0.82) |

AUDIOGRAM CLASSIFICATION SYSTEM

FIELD OF THE INVENTION

The invention relates to audiograms. In particular, the invention relates to a system for classifying audiograms.

BACKGROUND OF THE INVENTION

Hearing tests are commonly given in two parts: an air-conduction test and a bone-conduction test. Results of these tests are displayed in the form of an audiogram. Audiograms are graphical representations of how well a person can perceive different sound frequencies. An audiologist gives an air-conduction test and/or a bone-conduction test and the results are displayed on an audiogram. During air-conduction testing, earphones are worn and the sound travels through the air into the ear canal to stimulate the eardrum and then the auditory nerve. The person taking the test is instructed to give some type of response such as raising a finger or hand, pressing a button, pointing to the ear where the sound was received, or saying "yes" to indicate that the sound was heard. The audiologist uses a calibrated machine called an audiometer to present tones at different frequencies (pitches) and at different intensity (loudness) levels. A tone at a particular frequency (something like a violin note) is presented to one ear, and its intensity is raised and lowered until the person no longer responds consistently. Then, another signal of a different frequency is presented to the same ear, and its intensity is varied until there is no consistent response. This procedure is commonly done for at least six frequencies. Then the other ear is tested in the same way.

During bone-conduction testing, a tone is introduced through a small vibrator placed on the temporal bone behind the ear (or on the forehead). This method by-passes blockage, such as wax or fluid, in the outer or middle ears and reaches the auditory nerve through vibration of skull bones. This testing operates in the same manner as the air-conduction testing and is done to measure functionality of the inner ear independent of the functionality of the outer and middle ears. The responses are also recorded on the audiogram. The audiologist then interprets the audiogram.

Audiograms take on many different forms, and audiologists often do not interpret a single audiogram in the same way. For a single ear, several variables (e.g., frequency selectivity of hearing loss, behavioral variability, and measurement error) can conspire to create an enormous number of possible audiograms. Applicant calculated the number of possible audiogram configurations for six air-conduction frequencies (octave frequencies 250-8000 Hz) and five bone conduction frequencies (octave frequencies 250-4000 Hz) with the following constraints:
  a. Air-conduction thresholds can take any value between −10 and 110 dB HL (except at 250 Hz where the upper limit is 90 dB HL);
  b. An air conduction threshold must be within 30 dB of the threshold at the next lowest frequency;
  c. Bone-conduction thresholds can take any value between −10 and 60 dB HL except at 250 Hz where the upper limit is 40 dB HL;
  d. A bone conduction threshold must be between −50 and 10 dB relative to the air conduction threshold at that frequency.

With these constraints, there are more than 376 billion possible audiograms for a single ear. For an air-conduction only audiogram, there are 3.62 million possibilities.

Since there are so many different audiogram possibilities, audiograms are very difficult to categorize. FIG. 1 illustrates an example of an audiogram that is difficult to categorize. In this audiogram, "X" indicates the left ear unmasked air-conduction, "Δ" indicates right ear masked air conduction, "[" indicates right ear masked bone conduction, and "]" indicates left ear masked bone conduction. Five expert audiologists each gave a different description of the right ear hearing loss configuration: flat, sloping, rising, trough, and other. All are reasonable descriptions. It is also difficult to describe the site of lesion for this audiogram. Most audiologists would characterize the hearing loss as sensorineural, but a mixed hearing loss cannot be completely ruled out.

FIG. 2 provides another example of a difficult to categorize audiogram. Three audiologists categorized the right ear configuration as flat and two categorized the configuration as sloping. Two audiologists considered the audiogram to be sloping because thresholds for high frequencies are at least 20 dB poorer than for low frequencies. Three audiologists were willing to overlook the thresholds at 6000 and 8000 Hz in favor of the more important 250-4000 Hz range and considered the audiogram to be flat. Either judgment is defensible.

As can be seen, audiologists often do not interpret a single audiogram in the same way. This makes it difficult to categorize audiograms by a concise and practical classification system. Audiogram classification systems have been attempted in the past. However, these systems have generally been unsuccessful. For example, some classification systems provide numerous categories, subcategories, labels, subscripts, and superscripts in order to accommodate for the numerous interpretations. However, a classification system having too many categories is not practical for clinical application. Other classification systems do not account for disagreement among audiologists. For example, some classification systems provide general rules for placing audiograms in categories but do not deal with the practical issue of assigning a category when audiologists disagree or when there are local irregularities that audiologists learn to ignore. Also, local irregularities sometimes occur on an audiogram, and many audiologists ignore these when classifying audiograms. Known classification systems do not take into account local irregularities.

It would be desirable to provide an audiogram classification system that has clinical applications. It would be particularly desirable to provide a concise and practical audiogram classification system that does not have an overwhelming number of categories. It would also be desirable to provide a classification system that maximizes the likelihood that the selected classification of the audiogram agrees with audiologists. It would also be desirable to provide a classification system that also accounts for local irregularities that audiologists often ignore.

When interpreting audiograms, audiologists often use personal and subjective rules. As a result, it is difficult to analyze and compare subjectively categorized audiograms. Thus, it would be desirable to provide a standardized classification system with a standardized, non-subjective set of rules, so that audiograms categorized can be accurately analyzed and compared in order to study hearing loss trends, to correlate hearing loss types with ear disease, and so on.

Audiograms are also classified by audiologists manually, rather than by an automated program. It would be desirable to provide an automated classification system, since such a system would be easier to administer and would provide more consistent results.

In clinical settings, once an audiogram has been generated, an audiologist typically prescribes a treatment. Often times, the recommended treatment is a hearing aid. A variety of hearing aid types are available and audiologists commonly select a type that works best with a given hearing loss category. It would be desirable to provide a classification system that correlates hearing loss categories with hearing aid types. In some cases, it would be desirable to provide an automated classification system that automatically produces a hearing aid prescription that is correlated to a particular audiogram classification.

SUMMARY OF THE INVENTION

A method for classifying an audiogram is provided. In some embodiments, the method comprises:

selecting a configuration from the group consisting of a normal configuration, a flat configuration, a sloping configuration, a rising configuration, a trough configuration, a peaked configuration, and an other configuration;

selecting a severity, the severity depending on the selected configuration, wherein no severity is selected for the normal configuration, wherein the severity for the flat configuration is selected from the group consisting of mild, moderate, severe, and profound, wherein the severity for the sloping configuration is selected from the group consisting of normal-mild, normal-moderate, normal-severe, mild-moderate, mild-severe, moderate-severe, and severe-profound, wherein the severity for the rising configuration is selected from the group consisting of mild-normal, moderate-normal, moderate-mild, severe-normal, severe-mild, severe-moderate, profound-severe, and profound, wherein the severity for the trough configuration is selected from the group consisting of mild, moderate and severe, wherein the severity for the peaked configuration is selected from the group consisting of mild, moderate and severe, wherein the severity for the other configuration is selected from the group consisting of mild, moderate and severe;

selecting a site of lesion from the group consisting of a conductive site of lesion, a sensorineural site of lesion, a mixed site of lesion, and a sensorineural/mixed site of lesion; and selecting a symmetry from the group consisting of a symmetrical symmetry and an asymmetrical symmetry.

In some cases, the selecting is performed by a judge. The judge can perform the selecting using subjective preferences or using a set of rules. In other cases, a software program performs the selecting using the set of rules. The set of rules preferably ignore local irregularities on an audiogram. The rules have also preferably been validated to maximize agreement between judges.

In some cases, the method further comprises generating a hearing aid prescription, wherein the hearing aid prescription is based on a selected configuration, severity, and/or site of lesion. One or more values can be obtained from the set of rules and inputted into a hearing aid prescription formula, the hearing aid prescription formula being configured to generate a hearing aid prescription. In some cases, the one or more values include air-conduction threshold averages and bone-conduction threshold averages.

In another embodiment, a method for classifying an audiogram is provided, the method comprising:

selecting a configuration from the group consisting of a normal configuration, a flat configuration, a sloping configuration, a rising configuration, a trough configuration, a peaked configuration, and an other configuration; and selecting a severity, the severity depending on the selected configuration, wherein no severity is selected for the normal configuration, wherein the severity for the flat configuration is selected from the group consisting of mild, moderate, severe, and profound, wherein the severity for the sloping configuration is selected from the group consisting of normal-mild, normal-moderate, normal-severe, mild-moderate, mild-severe, moderate-severe, and severe-profound, wherein the severity for the rising configuration is selected from the group consisting of mild-normal, moderate-normal, moderate-mild, severe-normal, severe-mild, severe-moderate, profound-severe, and profound, wherein the severity for the trough configuration is selected from the group consisting of mild, moderate and severe, wherein the severity for the peaked configuration is selected from the group consisting of mild, moderate and severe, wherein the severity for the other configuration is selected from the group consisting of mild, moderate and severe, wherein the configuration and the severity are selected using rules based on at least one variable selected from the group consisting of a threshold average, moving threshold averages, mean of moving threshold averages, a maximum threshold, a minimum threshold, a maximum moving threshold average, and a minimum moving threshold average.

The method can further include selecting the normal configuration using rules based on the threshold average, the moving threshold averages, and the maximum moving threshold average. The method can also further include selecting the flat configuration using rules based on the moving threshold averages, the maximum threshold, the minimum threshold, the maximum moving threshold average, and the minimum moving threshold average. The selecting a severity for the flat configuration can be done using rules based the threshold average.

The method can further include selecting the sloping configuration using rules based on the moving threshold averages, the maximum moving threshold average, and the minimum moving threshold average. The selecting a severity for the sloping configuration can be done using rules based on moving threshold averages for a first frequency region and a second frequency region, wherein the second frequency region is higher than the first frequency region.

The method can further include selecting the rising configuration using rules based on the moving threshold averages, the maximum moving threshold average, and the minimum moving threshold average. The selecting a severity for the rising configuration can be done using rules based on moving threshold averages for a first frequency region and a second frequency region, wherein the second frequency region is higher than the first frequency region.

The method can further include selecting the trough configuration using rules based on the moving threshold averages and the maximum moving threshold average. The selecting a severity for the trough configuration can be done using rules based on the maximum moving threshold average.

The method can further include selecting the peaked configuration using rules based on the moving threshold averages and the maximum moving threshold average. The selecting a severity for the peaked configuration can be done using rules based on the threshold average.

The method can further include selecting the other configuration when rules for the normal configuration, the flat configuration, the sloping configuration, the rising configuration, the trough configuration, and the peaked configuration are not satisfied. The selecting a severity for the other configuration can be done using rules based on the threshold average.

The method can further include generating a hearing aid prescription, wherein the hearing aid prescription is based on a selected configuration, severity, and/or site of lesion. Likewise, the method can further include using one or more variables obtained from the rules in a hearing aid prescription formula, the hearing aid prescription formula being configured to generate a hearing aid prescription.

In another embodiment, a method of studying hearing losses is provided, the method comprising:

classifying a set of audiograms using an audiogram classification system, wherein the audiogram classification system includes configuration categories and severity categories, wherein the configuration categories include a normal configuration category, a flat configuration category, a sloping configuration category, a rising configuration category, a trough configuration category, a peaked configuration category, and an other configuration category, wherein the severity categories depend on the configuration categories and include (a) a mild category, a moderate category, a severe category, and a profound category for the flat configuration category, (b) a normal-mild category, normal-moderate category, normal-severe category, mild-moderate category, mild-severe category, moderate-severe category, and severe-profound category for the sloping configuration category, (c) a mild-normal category, a moderate-normal category, a moderate-mild category, a severe-normal category, a severe-mild category, a severe-moderate category, a profound-severe category, and a profound category for the rising configuration category, (d) a mild category, a moderate category, and a severe category for the trough configuration category, (e) a mild category, a moderate category, and a severe category for the peaked configuration category, and (f) a mild category, a moderate category, and a severe category for the other configuration category; and analyzing classified audiograms to evaluate hearing loss trends.

The audiogram classification system in this method can further include site of lesion categories, wherein the site of lesion categories include a conductive category, a sensorineural category, a mixed category and a mixed/sensorineural category. The system can also include symmetry categories, wherein the symmetry categories include a symmetrical category and an asymmetrical category.

In another embodiment, a method for classifying an audiogram is provided, the method comprising selecting a configuration using rules that incorporate variables, the variables including a threshold average, moving threshold averages, a mean of moving threshold averages, a maximum threshold, a minimum threshold, a maximum moving threshold average, and a minimum moving threshold average. The selecting a configuration can include selecting a configuration from the group consisting of a normal configuration, a flat configuration, a sloping configuration, a rising configuration, a trough configuration, a peaked configuration, and an other configuration.

The method can further include selecting a severity, the severity depending on the selected configuration, wherein no severity is selected for the normal configuration, wherein the severity for the flat configuration is selected from the group consisting of mild, moderate, severe, and profound, wherein the severity for the sloping configuration is selected from the group consisting of normal-mild, normal-moderate, normal-severe, mild-moderate, mild-severe, moderate-severe, and severe-profound, wherein the severity for the rising configuration is selected from the group consisting of mild-normal, moderate-normal, moderate-mild, severe-normal, severe-mild, severe-moderate, profound-severe, and profound, wherein the severity for the trough configuration is selected from the group consisting of mild, moderate and severe, wherein the severity for the peaked configuration is selected from the group consisting of mild, moderate and severe, wherein the severity for the other configuration is selected from the group consisting of mild, moderate and severe.

The method can further include selecting a site of lesion, wherein the site of lesion is selected from the group consisting of a conductive site of lesion, a sensorineural site of lesion, a mixed site of lesion, and a sensorineural/mixed site of lesion. Likewise, the method can further include selecting a symmetry, wherein the symmetry is selected from the group consisting of symmetrical and asymmetrical.

An automated audiogram classification system is also provided in accordance with one embodiment, the classification system comprising:

categories for configuration, severity, site of lesion and/or symmetry of an audiogram;

a set of rules for selecting the categories, wherein the set of rules ignore one or more local irregularities on an audiogram, wherein the set of rules have been validated to maximize agreement with judges; and a software program that classifies an audiogram using the set of rules.

In one embodiment, the set of rules for selecting the categories for configuration are based on one or more variables selected from the group consisting of a threshold average, moving threshold averages, a mean of moving threshold averages, a maximum threshold, a minimum threshold, a maximum moving threshold average, and a minimum moving threshold average. The categories for configuration can include a normal configuration category, a flat configuration category, a sloping configuration category, a rising configuration category, a trough configuration category, a peaked configuration category, and an other configuration category.

Likewise, the categories for severity can depend on the categories for configuration and wherein the categories for severity include (a) a mild category, a moderate category, a severe category, and a profound category for the flat configuration category, (b) a normal-mild category, normal-moderate category, normal-severe category, mild-moderate category, mild-severe category, moderate-severe category, and severe-profound category for the sloping configuration category, (c) a mild-normal category, a moderate-normal category, a moderate-mild category, a severe-normal category, a severe-mild category, a severe-moderate category, a profound-severe category, and a profound category for the rising configuration category, (d) a mild category, a moderate category, and a severe category for the trough configuration category, (e) a mild category, a moderate category, and a severe category for the peaked configuration category, and (f) a mild category, a moderate category, and a severe category for the other configuration category.

Also, the categories for site of lesion can include a conductive site of lesion category, a sensorineural site of lesion category, a mixed site of lesion category, and a sensorineural/mixed site of lesion category. The set of rules for selecting the categories for site of lesion can be based on one or more variables selected from the group consisting of a number of bone conduction thresholds exceeding a given value, a number off air-conduction thresholds exceeding a given value, a number of air-bone gaps exceeding a given size, and occurrences of bone-conduction threshold no responses.

Further, the categories for symmetry can include a symmetrical symmetry and an asymmetrical symmetry. The set of rules for selecting the categories for symmetry can be based on one or more variables selected from the group consisting of differences between a left ear threshold and a right ear threshold at a given frequency and a number of the differences exceeding a given value.

In some embodiments, each combination of the categories for configuration, severity, site of lesion and/or symmetry is linked to a hearing aid prescription. One or more values obtained from the set of rules can be further inputted into a hearing aid prescription formula, the hearing aid prescription formula being configured to generate a hearing aid prescription. In certain cases, the one or more values include air-conduction threshold averages and bone-conduction threshold averages.

BRIEF DESCRIPTION OF THE DRAWINGS

FIG. 3 is a table of audiogram classification system categories, in accordance with one embodiment;

FIG. 4 is a table of variables used in conjunction with the rules for categorizing configuration and severity shown in FIG. 5, in accordance with one embodiment;

FIG. 5 is a table of the rules for categorizing configuration and severity of an audiogram, in accordance with one embodiment;

FIG. 6 is a table of the rules for categorizing site of lesion of an audiogram, in accordance with one embodiment;

FIG. 7 is a table of the rules for categorizing symmetry of an audiogram, in accordance with one embodiment;

FIG. 8 is a table showing data on interjudge agreement obtained from a validation study of an audiogram classification system;

FIG. 9 is a table showing agreement pairs used in a validation study of an audiogram classification system;

FIG. 10 is a table showing data on agreement between judges and an audiogram classification system obtained from a validation study of an audiogram classification system;

DETAILED DESCRIPTION OF THE PREFERRED EMBODIMENTS

The following detailed description is to be read with reference to the drawings, in which like elements in different drawings have like reference numbers. The drawings, which are not necessarily to scale, depict selected embodiments and are not intended to limit the scope of the invention. Skilled artisans will recognize that the given examples have many alternatives that fall within the scope of the invention.

The invention provides an improved audiogram classification system that maximizes the likelihood that the selected category agrees with audiologists. The classification also ignores local irregularities that audiologists typically ignore. The classification system is useful for grouping audiograms to facilitate studies of relationships between audiogram configurations and ear disease. The classification system also produces a concise verbal description of the hearing loss to facilitate communication among professionals and between clinicians and patients. The classification system can also be implemented into a software program that can be incorporated into audiometer software or serve as a stand alone or web-based tool. The software program makes the classification system automated, so the audiogram can be classified without any human analysis. The classification system can also provide a hearing aid prescription that is correlated to a particular audiogram classification.

Figure 1:
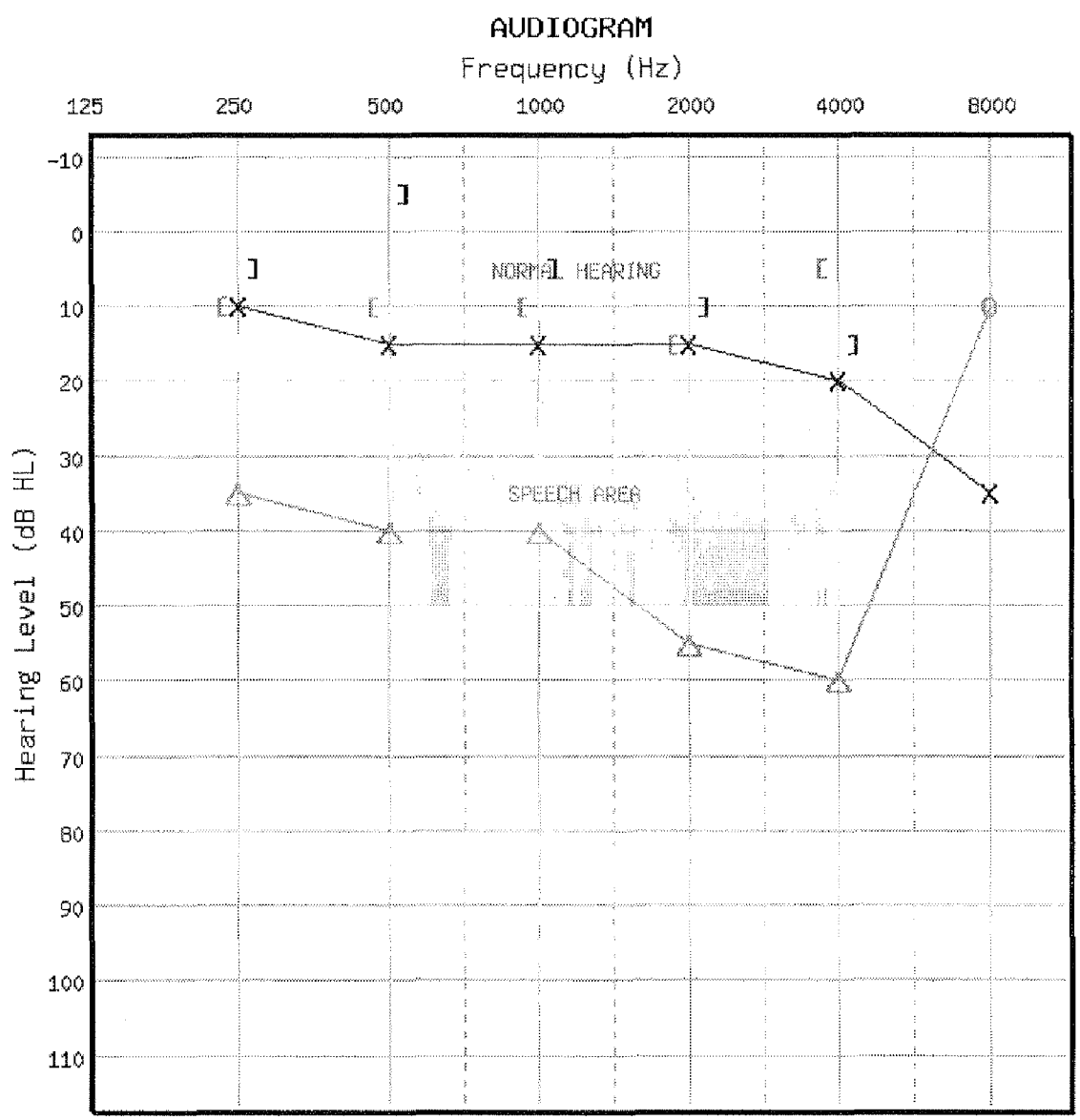
FIG. 1 is an illustration of one difficult to categorize audiogram.
Figure 2:
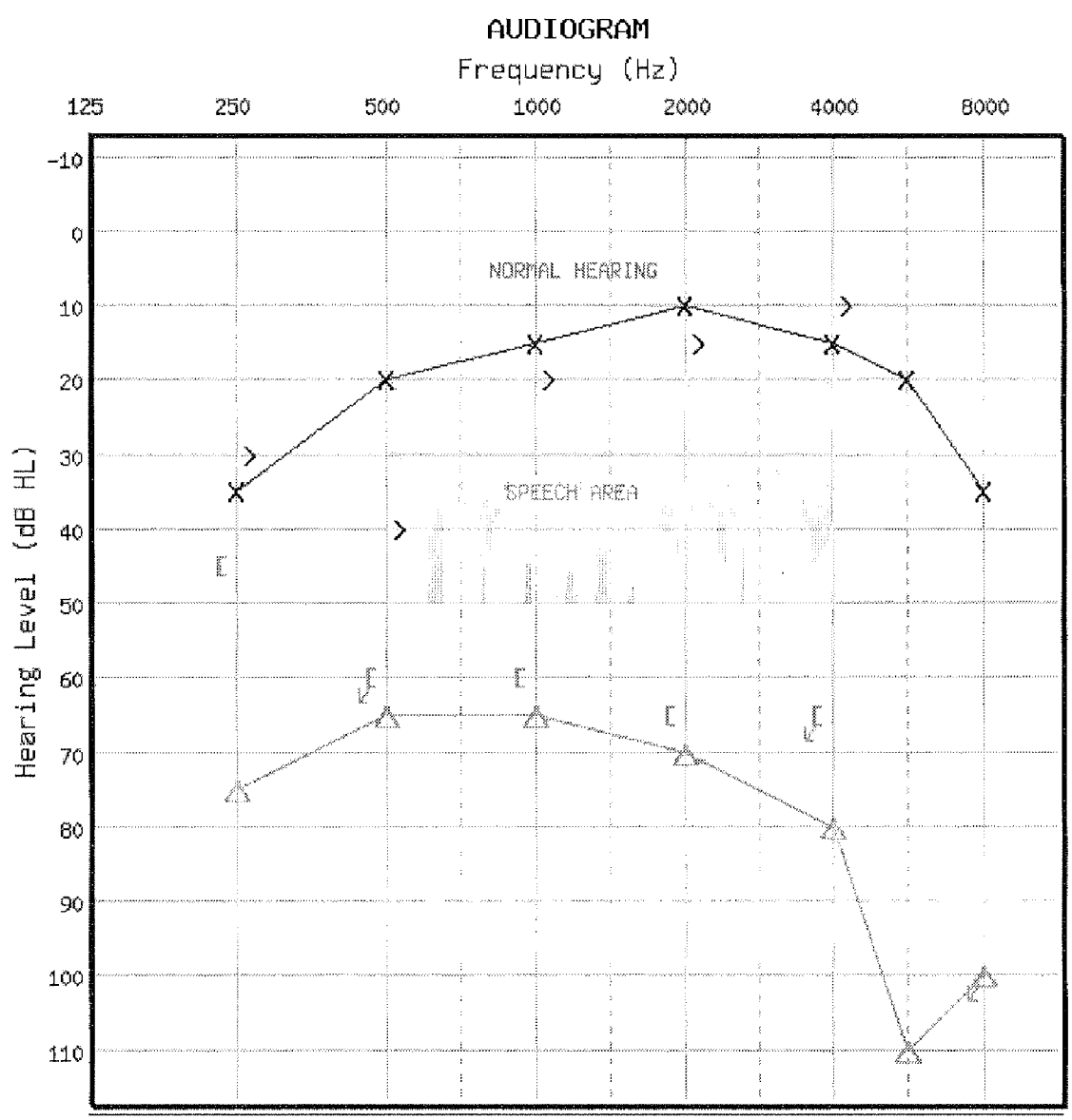
FIG. 2 is an illustration of another difficult to categorize audiogram.

The classification system provides categories for any standard audiogram. A standard audiogram is one that includes air-conduction thresholds at six octave frequencies (250-8000 Hz) and interoctave frequencies if available, and bone-conduction thresholds at five octave frequencies (250-4000 Hz). On a standard audiogram (for example an audiogram as shown in FIGS. 1 and 2), each line from left to right represents a pitch or frequency in Hertz (Hz) starting with the lowest pitches on the left side to the very highest frequencies tested on the right side. The range of frequencies tested by the audiologist are often 250 Hz, 500 Hz, 1000 Hz, 2000 Hz, 4000 Hz and 8000 Hz. Of course, any range of frequencies can be tested. Each line on the audiogram from top to bottom represents loudness or intensity in units of decibels (dB). Lines at the top of the chart (small numbers starting at minus 10 dB and 0 dB) represent soft sounds. Lines at the bottom of the chart (large numbers such as 100 dB and 110 dB) represent very loud sounds. Threshold measurements can be defined at a specific level or can be "No Response" at the output limit of the audiometer.

The categories for the classification system are illustrated in FIG. 3. Audiograms can be classified according to four general characteristics: (1) configuration, (2) severity, (3) site of lesion, and (4) symmetry. If only air-conduction thresholds are available, any configuration and severity categories are determined. The severity category is also dependent on the configuration category. If both air-conduction and bone-conduction thresholds are available, a site of lesion category is also determined. If air-conduction thresholds for both ears are available, a symmetry category is also determined. The classification system includes a very manageable number of categories, making the system practical for use in clinical applications. Each category will be described in detail below.

(1) Configuration

Configuration refers to the extent of hearing loss at each frequency and the overall picture of hearing that is created. For example, a hearing loss that only affects the high frequencies would be described as a high-frequency loss. Its configuration would show good hearing in the low frequencies and poorer hearing in the high frequencies. On the other hand, if only the low frequencies are affected, the configuration would show poor hearing for low frequencies and better hearing for high frequencies. The configuration category is further limited to the following seven subcategories: (a) normal, (b) flat, (c) sloping, (d) rising, (e) trough, (f) peaked, and (g) other. These configuration subcategories capture a large majority of patterns seen in clinical populations without resorting to an unwieldy number. Each subcategory will be described in further detail. The configuration subcategories are also determined by looking at the trends at the lower frequencies, middle frequencies, and high frequencies. As used herein, the terms low frequencies (or low frequency region) means 250-500 Hz, middle frequencies (or middle frequency region) means 750-3000 Hz, and high frequencies (or high frequency region) means 4000-8000 Hz.

(a) Normal

A normal configuration means that a person needs the same amount of loudness to hear at low, middle, or high frequencies. In one embodiment, an audiogram with a normal configuration is an audiogram that displays thresholds lower than or equal to 20 dB with some local deviations in thresholds allowed across different frequencies.

(b) Flat

A flat configuration means that a person needs the same amount of loudness to hear at low, middle, or high frequencies. In one embodiment, an audiogram with a flat configuration displays thresholds higher than or equal to 20 dB, but with some local deviations in thresholds allowed across different frequencies. For example, the allowable deviation can be within a 20 dB range across different frequencies.

(c) Sloping

A sloping configuration means that a person shows better hearing in the low frequencies. An audiogram with a sloping configuration displays a generally downward trend in thresholds. That is, thresholds are low in the low frequencies but become higher in the high frequencies. A sloping configuration can be flat in some regions or even rising if the general trend is downward. Such flat or rising deviations from the general trend are considered local irregularities that audiologists often ignore.

(d) Rising

A rising configuration means that a person shows better hearing in the high frequencies. An audiogram with a rising configuration displays a generally upward trend in thresholds. Rising is similar to sloping but in the reverse direction. Thresholds are higher in the low frequencies but become lower in the higher frequencies. A rising configuration can be flat in some regions or even sloping if the general trend is upward. Such flat or sloping deviations from the general trend are considered local irregularities that audiologists often ignore.

(e) Trough

A trough configuration means that a person shows better hearing in the high frequencies and low frequencies than in the middle frequencies. An audiogram with a trough configuration displays a dip in thresholds in the middle frequencies. The mid-frequency dip must be a clear trend not a local deviation.

(f) Peaked

A peaked configuration means that a person shows better hearing in the middle frequencies than the high frequencies and low frequencies. An audiogram with a peaked configuration displays a peak in thresholds in the middle frequencies. Peaked is similar to trough but with best hearing in the middle frequencies.

(g) Other

Other is a category for audiograms that are not consistently placed in any of the above categories by audiologists.

(2) Severity

Severity refers to the degree of hearing loss. Severity is described in terms of normal, mild, moderate, severe, and profound. In one embodiment, an audiogram is considered normal if thresholds are less than or equal to 20 dB. An audiogram is considered mild if thresholds are greater than 20 dB but less than or equal to 40 dB, moderate if thresholds are greater than 40 dB but less than or equal to 60 dB, severe if thresholds are greater than 60 dB but less than or equal to 90 dB, and profound if thresholds are greater than 90 dB.

In the present classification system, the severity category is dependent on the configuration category that is chosen. With reference to FIG. 3, if the audiogram is categorized as having a flat configuration, it can be further placed in one of four severity categories: mild, moderate, severe, or profound. If the audiogram is categorized as having a sloping configuration, it can be further placed in one of seven severity categories: normal-mild, normal-moderate, normal-severe, mild-moderate, mild-severe, moderate-severe, or severe-profound. If the audiogram is categorized as having a rising configuration, it can be further placed in one of eight severity categories: mild-normal, moderate-normal, moderate-mild, severe-normal, severe-mild, severe-moderate, profound-severe, or profound. In the sloping and rising configurations, severity is determined for each the low frequency and high frequency regions. If the audiogram is categorized as having a trough, peaked, or other configuration, it can be further placed in one of three severity categories: mild, moderate, or severe. The severity of peaked and trough-shaped hearing losses can be determined from thresholds in the region of best or worst hearing, respectively.

(3) Site of Lesion

Site of lesion refers to the type of hearing loss. The site of lesion category is determined independently of other categories and is further limited to the following four subcategories: (a) conductive, (b) sensorineural, (c) sensorineural, or (d) sensorineural or mixed. The type of hearing loss is determined from the differences between the air-conduction testing and the bone-conduction testing on an audiogram. These differences are referred to as air-bone gaps. The site of lesion category can be based on the presence of air-bone gaps at octave frequencies between 500 and 4000 Hz (e.g., at frequencies of 500, 1000, 2000, and 4000 Hz). Rules can be developed to determine whether an air-bone gap is present. Any rule can be used here, so long as the rule maximizes agreement between audiologists. In some embodiments, the 250 Hz frequency is not observed because of measurement errors observed at that frequency (e.g., errors due to vibrotactile responses and the lower audiometer output limit at that frequency). Each site of lesion category is discussed in further detail below.

(a) Conductive

A conductive loss refers to a decrease in sound caused by a problem in the outer or middle ear. Such a loss indicates normal inner ear activity. Conductive hearing loss occurs when sound is not conducted efficiently through the outer ear canal to the eardrum and the tiny bones, or ossicles, of the middle ear. An audiogram can be classified as conductive when air-bone gaps occur at various frequencies.

(b) Sensorineural

A sensorineural loss refers to a problem located in the inner ear (cochlea) or along the nerve pathway between the inner ear and the brain (retrocochlear). This type of loss may be caused by aging, infection or other disease, noise exposure, or it may be related to a genetic disorder. Sensorineural hearing loss not only involves a reduction in sound level, or ability to hear faint sounds, but also affects speech understanding, or ability to hear clearly. An audiogram can be classified as sensorineural when few or no air-bone gaps occur.

(c) Mixed

Sometimes a conductive hearing loss occurs in combination with a sensorineural hearing loss. In other words, there may be damage in the outer or middle ear and in the inner ear (cochlea) or auditory nerve. When this occurs, the hearing loss is referred to as a mixed hearing loss. An audiogram can be classified as mixed when an air- and bone-conduction hearing loss is shown and an air-bone gap exists.

(d) Sensorineural/Mixed

The sensorineural/mixed (as used herein, the term "sensorineural/mixed" means sensorineural or mixed) site of lesion category was included to describe audiograms where there is no response by bone conduction at the audiometer limit. In these cases, it is not possible to rule out a conductive component. The sensorineural or mixed category is intended for severe hearing losses for which bone conduction thresholds cannot be determined because of equipment limitations. An audiogram can be classified as sensorineural or mixed when an air-bone gap exists and one or more bone-conduction thresholds can't be determined.

(4) Symmetry

A symmetrical hearing loss means that the degree and configuration of hearing loss are the same in each ear. An asymmetrical hearing loss is one in which the degree and/or configuration of the loss is different for each ear. The symmetry category is limited to the following two subcategories: (1) symmetric or (2) asymmetric. An audiogram can be classified as asymmetric if there is a significant difference between air-conduction thresholds for the two ears. The determination of asymmetry, of course, requires a criterion for deciding if interaural threshold differences are significant. This criterion can be based on threshold averages, moving threshold averages, individual thresholds, or a combination. Any criterion or rule can be used, so long as it maximizes agreement between audiologists. In certain embodiments, the implemented rule takes into consideration the number of frequencies at which a particular difference occurs. A small but consistent difference at all frequencies may be considered asymmetrical. Likewise, if a difference occurs at fewer frequencies, the differences must be larger to be considered asymmetrical.

The process of determining the categories shown in FIG. 3 will now be described. In some cases, audiologists will simply select categories based on the chart provided in FIG. 3. The audiologists can simply use subjective rules they use in their clinical practices for interpreting the audiogram, so long as a category on FIG. 3 is ultimately selected. For example, an audiologist would first place the audiogram in one of the configurations categories. Once the configuration is determined the audiologist then determines the severity category. Again, the severity category depends on the configuration category. For example, if an audiologist determines the configuration to be sloping, the audiologist then selects a severity from the following categories: normal-mild, normal-moderate, normal-severe, mild-moderate, mild-severe, moderate-severe, or severe-profound. In another example, if an audiologist determines the configuration to be peaked, the judge then selects a severity from the following categories: mild, moderate and severe. The audiologist can then place the audiogram in a site of lesion category. The site of lesion category is independent from the other categories. The audiologist can then place the audiogram in a symmetry category. The symmetry category is also independent from the other categories. Even though audiologists are using their own rules, the set of categories of the audiogram is standardized. All audiograms categorized by this method can be analyzed and compared to study hearing loss trends and other things.

In certain embodiments, the category selection is done using a specific set of rules. Either an audiologist manually categorizes the audiogram using the rules or the rules are incorporated into a software program. The software can use the rules to automatically place the audiogram into the described categories. This allows for an automated classification system.

The rules can be selected to maximize the likelihood that the selected categories agree with audiologists. For example, rules can be developed and then validated against opinions of audiologists. The rules can be designed to ignore local irregularities that experienced audiologists generally overlook. Local irregularities are herein defined as thresholds that do not follow the trend of those thresholds at neighboring frequencies. Embodiments of specific rules will be described in detail below.

FIGS. 4-7 illustrate the classification rules according to one embodiment. The classification rules will now be described in further detail.

Rules for Configuration and Severity

The configuration rules can be based on air-conduction variables such as threshold averages, moving threshold averages, mean of moving averages, maximum thresholds, minimum thresholds, maximum moving average, minimum moving average, and so on. A threshold average is an average or mean for thresholds at selected frequencies. A moving threshold average is an average or mean for thresholds at selected overlapping frequencies. A mean of moving averages is defined as the mean for one or more selected moving averages. A maximum threshold is the maximum of one or more thresholds at selected frequencies. A minimum threshold is the minimum of one or more thresholds at selected frequencies. A maximum moving average is the maximum of one or more selected moving averages. A minimum moving average is the minimum of one or more selected moving averages. These variables are used to capture the configuration and severity of an audiogram without being overly sensitive to local irregularies that depart from the overall audiogram pattern. The severity rules can be based on variables such as threshold averages, moving averages, and maximum moving threshold average. When configuration and severity rules incorporate one or more of these variables, they are in a way that captures the overall severity without undue influence by local irregularities, i.e., individual thresholds that don't adhere to the overall trend. Rules based on several variables also help ensure that the selected configuration or severity agrees with audiologists.

FIGS. 4 and 5 illustrate the rules used to determine a configuration and severity category, according to one specific embodiment. After an audiogram is generated, the audiogram parameters obtained from air-conduction testing are used to calculate the variables shown in FIG. 4. Variables A, B, C, D, E, F, and G are moving threshold averages. Each stands for a mean of certain overlapping frequencies. For example, variable A is a mean of thresholds 250 Hz and 500 Hz. Variable B is a mean of thresholds 250 Hz, 500 Hz, 750 Hz, and 1000 Hz. Variable C is a mean of thresholds 500 Hz, 750 Hz, 1000 Hz, 1500 Hz, and 2000 Hz. Variable D is a mean of thresholds 1000 Hz, 1500 Hz, 2000 Hz, 3000 Hz, and 4000 Hz. Variable E is a mean of thresholds 2000 Hz, 3000 Hz, 4000 Hz, 6000 Hz, and 8000 Hz. Variable F is a mean of thresholds 4000 Hz, 6000 Hz, and 8000 Hz. Variable H stands for a moving threshold average of A or B or C. Variable I stands for a moving threshold average of E or F or G. Variable J is a maximum threshold average of thresholds 4000 Hz, 6000 Hz, or 8000 Hz. Variable K is a sum of the maximum and minimum moving threshold averages for variables A, B, C, D, or E. Variable MAMin is a minimum moving threshold average for variables A, B, C, D, E, or F. Variable MAMax is a maximum moving threshold average for variables A, B, C, D, E or F. Variable L is a sum of differences between the minimum threshold and the thresholds in the low- and high-frequency regions. Variable Av is a mean of thresholds 500 Hz, 750 Hz, 1000 Hz, 1500 Hz, 2000 Hz, 3000 Hz, or 4000 Hz. Variable AV1 is a mean of moving threshold averages for variables A, B, C, D, E, F, and G. Variable Tmax is a maximum threshold for 500 Hz, 750 Hz, 1000 Hz, 2000 Hz, 3000 Hz, or 4000 Hz. Variable Tmin is a minimum threshold for 500 Hz, 750 Hz, 1000 Hz, 2000 Hz, 3000 Hz, or 4000 Hz.

The variables shown in FIG. 4 are inputted into the rules shown in FIG. 5. The rules in FIG. 5 determine whether the audiogram shows a normal configuration, a flat configuration, a sloping configuration, a rising configuration, a trough-shaped configuration, a peaked configuration, or other. The rules also further classify the severity of each configuration. The rules will now be described in detail.

Normal Configuration

In the illustrated embodiment, rules for determining whether an audiogram shows a normal configuration are based on a threshold average (Av), moving threshold averages (B, E), and a maximum moving threshold average (MAMax). A normal configuration is shown if: Av<=20 and B<=20 and E<=25 and MAMax<23. In other words, a normal configuration for the audiogram is selected when the audiogram displays air-conduction thresholds having: (1) a mean of less than or equal to 20 dB at frequencies of 500 Hz, 750 Hz, 1000 Hz, 1500 Hz, 2000 Hz, 3000 Hz and 4000 Hz; (2) a mean of less than or equal to 20 dB at frequencies of 250 Hz, 500 Hz, 750 Hz, and 1000 Hz; (3) a mean of less than or equal to 25 dB at frequencies of 2000 Hz, 3000 Hz, 4000 Hz, 6000 Hz, and 8000 Hz; and (4) a MAMax of less than or equal to 23 dB, wherein MAMax is a maximum mean selected from the group consisting of a mean for frequencies of 250 Hz, 500 Hz, 750 Hz, and 1000 Hz, a mean for frequencies of 500 Hz, 750 Hz, 1000 Hz, 1500 Hz, and 2000 Hz, a mean or frequencies of 1000 Hz, 1500 Hz, 2000 Hz, 3000 Hz, and 4000 Hz, a mean for frequencies of 2000 Hz, 3000 Hz, 4000 Hz, 6000 Hz, and 8000 Hz, and a mean for frequencies of 4000 Hz, 6000 Hz, and 8000 Hz.

Severity for Normal Configuration

If a normal configuration is selected, a severity is not determined.

Flat Configuration

In the illustrated embodiment, rules for determining whether an audiogram shows a flat configuration are based on moving threshold averages (A, B, C, D, E, F), a maximum threshold (Tmax), a minimum threshold (Tmin), a maximum moving threshold average (MAMax), a minimum moving threshold average (MAMin), and a sum of the maximum and minimum moving threshold averages for threshold averages A, B, C, D, or E (K). A flat configuration is shown if [K<=15 or |A-F|<=15] and MAmax-F<15 and C-F>-30 and Tmax-Tmin<25 (500-4000). A flat configuration is not shown if MAmax-A>7.4 and MAmax-F>7.4; or A-MAMin>7.4 and G-MAMin>10 and L>33; or A<20 and B<20 and C<20 and D>=20 and E>21 and F>27; or A>20 and B>20 and D<17.5 and E<15 and F<=15.

In other words, a flat configuration for the audiogram is selected when all of the following take place: (a) K is less than or equal to 15 dB or the mean of A, B, C, D, E, and F is less than or equal to 15 dB, wherein K is the maximum of A, B, C, D, or E plus the minimum of A, B, C, D, or E, wherein A is the mean threshold for frequencies of 250 Hz and 500 Hz, wherein B is the mean threshold for frequencies of 250 Hz, 500 Hz, 750 Hz, and 1000 Hz, wherein C is the mean threshold for frequencies of 500 Hz, 750 Hz, 1000 Hz, 1500 Hz, and 2000 Hz, wherein D is the mean threshold for frequencies of 1000 Hz, 1500 Hz, 2000 Hz, 3000 Hz, and 4000 Hz, wherein E is the mean threshold for frequencies of 2000 Hz, 3000 Hz, 4000 Hz, 6000 Hz, and 8000 Hz, and wherein F is the mean threshold for frequencies of 4000 Hz, 6000 Hz, and 8000 Hz; (b) MAmax minus F is less than 15, wherein MAmax is the maximum of A, B, C, D, E, or F; (c) C minus F is greater than −30; and (d) Tmax−Tmin is less than 25, wherein Tmax is the maximum threshold for frequencies of 500 Hz, 750 Hz, 1000 Hz, 1500 Hz, 2000 Hz, 3000 Hz, or 4000 Hz and wherein Tmin is the minimum threshold for frequencies of 500 Hz, 750 Hz, 1000 Hz, 1500 Hz, 2000 Hz, 3000 Hz, or 4000 Hz.

The flat configuration is not selected when any of the following take place: (a) MAmax minus A is greater than 7.4 dB and MAMax minus F is greater than 7.4 dB; (b) A minus MAMin is greater than 7.4 dB and G minus MAMin is greater than 10 dB and L is greater than 33 dB, wherein MAMin is the minimum of A, B, C, D, E, or F, wherein G is the mean threshold for frequencies of 600 Hz and 8000 Hz, and wherein L is (A minus MAMin)+(B minus MAMin)+(G minus MAMin); (c) A is less than 20 dB, B is less than 20 dB, C is less than 20 dB, D is greater than or equal to 20 dB, E is greater than 21 dB, and F is greater than 27; or (d) A is greater than 20 dB, B is greater than 20 dB, D is less than 17.5 dB, E is less than 15 dB and F is less than or equal to 15 dB.

Severity of Flat Configuration

Once a flat configuration is selected, the severity is next determined. In the illustrated embodiment, rules for determining severity of a flat configuration are based on a threshold average (Av). The severity for the flat configuration is selected as mild if Av<40, as moderate if 40<=Av<60, as severe if 60<=Av<88, or as profound if Av>=88. In other words, the severity is selected as mild when a threshold average for frequencies of 500 Hz, 750 Hz, 1000 Hz, 2000 Hz, 3000 Hz, or 4000 Hz is less than 40 dB, selected as moderate when the threshold average is greater than or equal to 40 dB but less than 60 dB, selected as severe when the threshold average is greater than or equal to 60 dB but less than 88 dB, and selected as profound when the threshold average is greater than or equal to 88 dB.

Sloping Configuration

In the illustrated embodiment, rules for determining whether an audiogram shows a sloping configuration are based on moving threshold averages (A, B, C, D, E, F, G), a maximum moving threshold average (MAMax), and a minimum moving threshold average (MAMin). A sloping configuration is shown if: A−F<−17 or [A<20 and B<20 and C<20 and D>=20 and E>21 and F>27]. A sloping configuration is not shown if: MAMax minus A>7.4 and [MAMax minus F>7.4 or MAMax minus G>12]; or A minus MAMin>7.4 and G minus MAMin>10 and A minus F>−45.

In other words, a sloping configuration is selected if any of the following takes place: (a) A minus F is less than −17 dB; or (b) A is less than 20 dB, B is less than 20 dB, C is less than 20 dB, D is greater than or equal to 20 dB, E is greater than 21 dB and F is greater than 27 Db, wherein A is the mean threshold for frequencies of 250 Hz and 500 Hz, wherein B is the mean threshold for frequencies of 250 Hz, 500 Hz, 750 Hz, and 1000 Hz, wherein C is the mean threshold for frequencies of 500 Hz, 750 Hz, 1000 Hz, 1500 Hz, and 2000 Hz, wherein D is the mean threshold for frequencies of 1000 Hz, 1500 Hz, 2000 Hz, 3000 Hz, and 4000 Hz, wherein E is the mean threshold for frequencies of 2000 Hz, 3000 Hz, 4000 Hz, 6000 Hz, and 8000 Hz, and wherein F is the mean threshold for frequencies of 4000 Hz, 6000 Hz, and 8000 Hz.

The sloping configuration is not selected when any of the following take place: (a) MAMax minus A is greater than 7.4 and [MAMax minus F is greater than 7.4 or MAMAx minus G is greater than 12], wherein MAMax is the maximum of A, B, C, D, E, or F and wherein G is the mean threshold for frequencies of 600 Hz and 8000 Hz; or (b) A minus MAMin is greater than 7.4 and G minus MAMin is greater than 10 and A minus F is greater than −45, wherein MAMin is the minimum of A, B, C, D, E, or F.

Severity of Sloping Configuration

If the audiogram is classified as sloping, the severity is determined as follows. In the illustrated embodiment, rules for determining severity of a sloping configuration are based on moving averages for a first frequency region and a second frequency region, wherein the second frequency region is higher than the first frequency region. For example, the first frequency region in the illustrated embodiment is represented by variable B for frequencies of 250 Hz, 500 Hz, 750 Hz, and 1000 Hz. The second frequency region is represented by variable F for frequencies of 4000 Hz, 6000 Hz, and 8000 Hz. The severity is selected as normal-mild when B is less than or equal to 20 dB and F is greater than 20 dB and less than 40 dB, selected as normal-moderate when B is less than or equal to 20 dB and F is greater than or equal to 40 dB and less than 61 dB, selected as normal-severe when B is less than or equal to 20 dB and F is greater than or equal to 61 dB, selected as mild-moderate when B is greater than 20 dB and less than or equal to 48 dB and F is greater than 40 dB and less than 61 dB, selected as mild-severe when B is greater than 20 dB and less than or equal to 48 dB and F is greater than or equal to 61 dB, selected as moderate-severe when B is greater than 48 dB and less than or equal to 65 dB and F is greater than or equal to 61 dB, selected as severe-profound when B is greater than 65 dB and less than 90 dB and F is greater than or equal to 90 dB, and selected as profound, when B is greater than or equal to 90 dB and F is greater than 105 dB.

Rising Configuration

In the illustrated embodiment, rules for determining whether an audiogram shows a rising configuration are based on moving threshold averages (A, C, D, E, F, G), a maximum moving threshold average (MAMax), and a minimum moving threshold average (MAMin). A rising configuration is shown if: MAMax−F>=15; or A>20 and B>20 and D<17.5 and E<15 and F<=15. A rising configuration is not shown if: MAMax−A>7.4 and MAMax−F>7.4; or A−MAMin>7.4 and G−MAMin>10. In other words, the rising configuration is selected when any of the following take place: (a) MAMax minus F is greater than or equal to 15; or (b) A is greater than 20, B is greater than 20, D is less than 17.5, E is less than 15, and F is less than or equal to 15, wherein A is the mean threshold for frequencies of 250 Hz and 500 Hz, wherein B is the mean threshold for frequencies of 250 Hz, 500 Hz, 750 Hz, and 1000 Hz, wherein C is the mean threshold for frequencies of 500 Hz, 750 Hz, 1000 Hz, 1500 Hz, and 2000 Hz, wherein D is the mean threshold for frequencies of 1000 Hz, 1500 Hz, 2000 Hz, 3000 Hz, and 4000 Hz, wherein E is the mean threshold for frequencies of 2000 Hz, 3000 Hz, 4000 Hz, 6000 Hz, and 8000 Hz, wherein F is the mean threshold for frequencies of 4000 Hz, 6000 Hz, and 8000 Hz, and wherein MAMax is the maximum of A, B, C, D, E, or F.

The rising configuration is not selected when any of the following take place: (a) MAMax minus A is greater than 7.4 and MAMax minus F is greater than 7.4; or (b) A minus MAMin is greater than 7.4 and G minus MAMin is greater than 10, wherein G is the mean threshold for frequencies of 600 Hz and 8000 Hz and wherein MAMin is the minimum of A, B, C, D, E, or F.

Severity for Rising Configuration

If the audiogram is classified as rising, the severity is determined as follows. In the illustrated embodiment, rules for determining severity of a rising configuration are based on moving averages for a first frequency region and a second frequency region, wherein the second frequency region is higher than the first frequency region. For example, the first frequency region in the illustrated embodiment is represented by variable A for frequencies of 250 Hz and 500 Hz. The second frequency region is represented by variable F for frequencies of 4000 Hz, 6000 Hz, and 8000 Hz. The severity is selected as mild-normal when A is greater than 25 dB and less than 40 dB and F is less than or equal to 25 dB, selected as moderate-normal when A is greater than or equal to 40 dB and less than 60 dB and F is less than or equal to 25 dB, selected as moderate-mild when A is greater than or equal to 40 dB and less than 60 dB and F is greater than 25 dB and less than 40 dB, selected as severe-normal when A is greater than or equal to 60 dB and less than 90 dB and F is less than or equal to 25, selected as severe-mild when A is greater than or equal to 60 dB and less than 90 dB and F is greater than 25 dB and less than 40 dB, selected as severe-moderate when A is greater than or equal to 60 dB and less than 90 dB and F is greater than or equal to 40 dB and less than 60 dB, selected as profound-severe when A is greater than or equal to 90 dB and F is greater than or equal to 60 dB and less than 90 dB, and selected as profound when A is greater than or equal to 90 dB and F is greater than or equal to 90 dB.

Trough Configuration

In the illustrated embodiment, rules for determining whether an audiogram shows a trough configuration are based on moving threshold averages (A, F, G) and a maximum moving threshold average (MAMax). A trough-shaped hearing loss is shown if MAMax−A>7.4 and [MAMax−F>7.4 or MAMax−G>12]. In other words, the trough configuration is selected when all of the following takes place: (a) MAMax minus A is greater than 7.4; and (b) MAMax minus F is greater than 7.4 or MAMAx minus G is greater than 12, wherein A is the mean threshold for frequencies of 250 Hz and 500 Hz, wherein B is the mean threshold for frequencies of 250 Hz, 500 Hz, 750 Hz, and 1000 Hz, wherein C is the mean threshold for frequencies of 500 Hz, 750 Hz, 1000 Hz, 1500 Hz, and 2000 Hz, wherein D is the mean threshold for frequencies of 1000 Hz, 1500 Hz, 2000 Hz, 3000 Hz, and 4000 Hz, wherein E is the mean threshold for frequencies of 2000 Hz, 3000 Hz, 4000 Hz, 6000 Hz, and 8000 Hz, wherein F is the mean threshold for frequencies of 4000 Hz, 6000 Hz, and 8000 Hz, wherein G is the mean threshold for frequencies of 600 Hz and 8000 Hz, and wherein MAMax is the maximum of A, B, C, D, E, or F.

Severity for Trough Configuration

If the audiogram is classified as trough-shaped, the severity is determined as follows. In the illustrated embodiment, rules for determining severity of a trough configuration are based on a maximum moving threshold average (MAMax). The maximum moving threshold average is the maximum of moving averages represented by variables A, B, C, D, E, or F. The trough-shaped audiogram is classified as mild when MAMax is greater than or equal to 20 dB and less than 40 dB, selected as moderate when MAMax is greater than or equal to 40 dB and less than 60 dB, and selected as severe when MAMax is greater than or equal to 60 dB.

Peaked Configuration

In the illustrated embodiment, rules for determining whether an audiogram shows a peaked configuration are based on moving threshold averages (A, G) and a maximum moving threshold average (MAMax). A peaked hearing loss is shown if A−MAMin>7.4 and G−MAMin>10 and L>33. In other words, the peaked configuration is selected when all of the following take place: (a) A−MAMin is greater than 7.4 dB; (b) G minus MAMin is greater than 10 dB, and (c) L is greater than 33 dB, wherein A is the mean threshold for frequencies of 250 Hz and 500 Hz, wherein B is the mean threshold for frequencies of 250 Hz, 500 Hz, 750 Hz, and 1000 Hz, wherein C is the mean threshold for frequencies of 500 Hz, 750 Hz, 1000 Hz, 1500 Hz, and 2000 Hz, wherein D is the mean threshold for frequencies of 1000 Hz, 1500 Hz, 2000 Hz, 3000 Hz, and 4000 Hz, wherein E is the mean threshold for frequencies of 2000 Hz, 3000 Hz, 4000 Hz, 6000 Hz, and 8000 Hz, wherein F is the mean threshold for frequencies of 4000 Hz, 6000 Hz, and 8000 Hz, wherein G is the mean threshold for frequencies of 600 Hz and 8000 Hz, wherein MAMax is the maximum of A, B, C, D, E, or F, wherein MAMin is the minimum of A, B, C, D, E, or F, and wherein L is (A minus MAMin) plus (B minus MAMin) plus (G minus MAMin).

Severity for Peaked Configuration

In the illustrated embodiment, rules for determining severity of a peaked configuration are based on a threshold average (Av). If the audiogram is classified as peaked-shaped, the severity is determined as follows. The peaked audiogram is classified as mild if Av<36, as moderate if 36<=Av<60, or as severe if Av>=60. In other words, the severity is selected as mild when an overall threshold average is less than 36 dB, selected as moderate when the overall threshold average is greater than or equal to 36 dB but less than 60 dB, or selected as severe when an overall threshold average is greater than or equal to 60 dB, wherein the overall threshold average is a mean for frequencies of 500 Hz, 750 Hz, 1000 Hz, 1500 Hz, 2000 Hz, 3000 Hz, and 4000 Hz.

Other Configuration

The other configuration is selected when none of the rules for the other categories are satisfied.

Severity for Other Configuration

In the illustrated embodiment, rules for determining severity of an other configuration are based on a threshold average (Av). If the audiogram is given an other configuration, the severity is determined as follows. The audiogram is classified as mild if Av<40, as moderate if 40<=Av<60, or as severe if Av>=60. In other words, the severity is selected as mild when an overall threshold average is less than 40 dB, selected as moderate when the overall threshold average is greater than or equal to 40 dB but less than 60 dB, or selected as severe when an overall threshold average is greater than or equal to 60 dB, wherein the overall threshold average is a mean for frequencies of 500 Hz, 750 Hz, 1000 Hz, 1500 Hz, 2000 Hz, 3000 Hz, and 4000 Hz. Thus, the configuration and severity of an audiogram is chosen using the above set of rules.

Rules for Site of Lesion

The site of lesion of an audiogram can next be determined using another set of rules, as shown in FIG. 6. The site of lesion determination is independent of the configuration, severity, and symmetry determination. Site of lesion categories are based on the difference between air-conduction and bone-conduction thresholds (air-bone gap). In general, normal hearing with no air-bone gap is classified as normal. When bone conduction hearing is normal and there is a hearing loss by air conduction the site of lesion is conductive. When there is a hearing loss and no air-bone gap, the hearing loss is sensorineural. A mixed hearing loss is one in which there is a hearing loss by air conduction, a hearing loss by bone-conduction, and an air-bone gap. The "sensorineural or mixed" category is intended for severe hearing losses for which bone conduction thresholds cannot be determined because of equipment limitations. In some cases, 250 Hz is not used in the determination of site of lesion because of measurement error that commonly occurs at that frequency.

The site of lesion rules shown in FIG. 6 will now be described in detail. In the illustrated embodiment, the site of lesion rules account for one or more of the following variables: number of bone conduction thresholds exceeding a given value, number of air-conduction thresholds exceeding a given value, number of air-bone gaps exceeding a given size, and occurrences of bone-conduction threshold no responses.

Conductive Site of Lesion

In the illustrated embodiment, the rules for determining whether an audiogram shows a conductive site of lesion are based on the number of bone conduction thresholds exceeding a given value, the number of air-conduction thresholds exceeding a given value, and the number of air-bone gaps exceeding a given size. An audiogram is classified as conductive if a number of conditions are satisfied. First, at least three out of four of the bone conduction thresholds at 500 Hz ($B_5$), 1000 Hz ($B_1$), 2000 Hz ($B_2$), and 4000 Hz ($B_4$) must be less than 25 dB or each of these thresholds must be less than 30 dB. If one of these two conditions occurs, it is then determined whether one of conditions A or B occurs. If either A or B occurs, the audiogram is classified as conductive. Condition A takes place if at least three out of four of the air-bone gaps at thresholds 500 Hz ($ABG_5$), 1000 Hz ($ABG_1$), 2000 Hz ($ABG_2$), and 4000 Hz ($ABG_4$) are of a size greater than or equal to 10 dB. Condition B takes place if at least one of the following conditions occur: (1) the air-bone gap at threshold 500 Hz ($ABG_5$) has a size is greater than or equal to 15 dB and each air conduction-threshold of 1000 Hz (T1), 2000 Hz (T2), or 4000 Hz (T4) is less than or equal to 20 dB, (2) the air-bone gap at threshold 1000 Hz ($ABG_1$) has a size is greater than or equal to 15 db and each air-conduction threshold of 500 Hz (T5), 2000 Hz (T20, or 4000 Hz (T4) is less than or equal to 20 dB, (3) the air-bone gap at threshold 2000 Hz ($ABG_2$) has a size is greater than or equal to 15 db and each air-conduction threshold of 500 Hz (T5, 1000 Hz (T1, or 4000 Hz (T4) is less than or equal to 20 dB, or (4) the air-bone gap at threshold 4000 Hz ($ABG_4$) has a size is greater than or equal to 15 dB and each air-conduction threshold of 500 Hz (T5), 1000 Hz (T1), or 2000 Hz (T2) is less than or equal to 20 dB. If one of these conditions occurs, condition B is satisfied and the hearing loss is classified as conductive.

Sensorineural Site of Lesion

In the illustrated embodiment, the rules for determining whether an audiogram shows a sensorineural site of lesion are based on the number of air-bone gaps exceeding a given size. With continued reference to FIG. 6, a hearing loss is classified as sensorineural only (and also ruling out the possibility of the hearing loss being normal or conductive) if either condition C or D takes place. Condition C takes place if at least three out of four of the air-bone gaps at thresholds 500 Hz ($ABG_5$), 1000 Hz ($ABG_1$), 2000 Hz ($ABG_2$), or 4000 Hz ($ABG_4$) are less than 10 dB or if at least one out of four of the air-bone gaps at the same thresholds are less than or equal to 15 dB. Condition D is satisfied if at least two out of four of the air-bone gaps at thresholds 500 Hz ($ABG_5$), 1000 Hz ($ABG_1$), 2000 Hz ($ABG_2$), or 4000 Hz ($ABG_4$) are less than 10 dB or if at least one out of four of the air-bone gaps at the same thresholds are less than or equal to 10 dB. If either condition C or D is satisfied, the audiogram is classified as sensorineural only.

Mixed Site of Lesion

In the illustrated embodiment, the rules for determining whether an audiogram shows a mixed site of lesion are based on the number of air-bone gaps exceeding a given size and the occurrences of bone-conduction threshold no responses. An audiogram is categorized as mixed only (and also ruling out the possibility of the hearing loss being normal, conductive, or sensorineural only) if condition E or F takes place. Condition E takes place if at least two out of four of the air-bone gaps at thresholds 500 Hz ($ABG_5$), 1000 Hz ($ABG_1$), 2000 Hz ($ABG_2$), or 4000 Hz ($ABG_4$) are both (a) greater than or equal to 10 dB and (b) have a bone-conduction threshold ≠NR. The term "NR" means there is no response at the maximum intensity the audiometer can produce for that frequency. The term "≠NR" means that a no response for a given intensity did not occur. The term "=NR" means that a no response for that intensity did occur. If condition E is satisfied, the hearing loss is classified as mixed. If condition E is not satisfied, it is determined whether condition F is satisfied. Condition F is satisfied if at least one out of four of the air-bone gaps at thresholds 500 Hz ($ABG_5$), 1000 Hz ($ABG_1$), 2000 Hz ($ABG_2$), or 4000 Hz ($ABG_4$) are both (a) greater than or equal to 15 dB and (b) have a bone-conduction threshold ≠NR. If either condition E or F is satisfied, the audiogram is classified as mixed.

Sensorineural/Mixed Site of Lesion

In the illustrated embodiment, the rules for determining whether an audiogram shows a mixed site of lesion are based on the number of air-bone gaps exceeding a given size and the occurrences of bone-conduction threshold no responses. An audiogram is classified as sensorineural or mixed (and also ruling out the possibility of the hearing loss being, normal, conductive, sensorineural or mixed) if at least one out of four of the air-bone gaps at thresholds 500 Hz ($ABG_5$), 1000 Hz ($ABG_1$), 2000 Hz ($ABG_2$), and 4000 Hz ($ABG_4$) are both (a) greater than or equal to 10 dB and (b) have bone conduction thresholds =NR.

Rules for Symmetry

The symmetry of an audiogram can also be determined. This determination is independent of the configuration, severity, and site of lesion determination. Symmetry is evaluated using air-conduction thresholds. In the illustrated embodiment, the symmetry rules account for one or more of the following variables: difference between the left ear and right ear thresholds at a given frequency and the number of differences exceeding a given value.

The symmetry rules shown in FIG. 7 will now be described in detail. An audiogram is classified as asymmetrical if at least one of conditions A or B or C or D or E or F or G occurs. Condition A occurs if |AvLt minus AvRt|>10, wherein Av is a mean air-conduction threshold for frequencies of 500 Hz (T500), 750 Hz (T750), 1000 Hz (T1000), 1500 Hz (T1500), 2000 Hz (T2000), 3000 Hz (T3000) and 4000 Hz (T4000) air-conduction thresholds. Condition B occurs if at least three of the following occurs: T250R minus T250L>5, T500R minus T500L>5, T1R minus T1L>5, T2R minus T2L>5, T4R minus T4L>5, or T8R minus T8L>5. Condition C occurs if at least three of the following occurs: T250L–T250R>5, T500L–T500R>5, T500L–T500R>5, T2L–T2R>5, T4L–T4R>5, or T8R–T8L>5. Condition D occurs if at least two of the following occurs: T250R–T250L>10, T500R–T500L>10, T500R–T500L>10, T2R–T2L>10, T4R–T4L>10, T8L–T8R>5. Condition E occurs if two of the following occurs: T250L–T250R>10, T500L–T500R>10, T500L–T500R>10, T2L–T2R>10, T4L–T4R>10, or T8R–T8L>10. Condition F occurs if one of the following occurs: T250R–T250L>15, T500R–T500L>15, T500R–T500L>15, T2R–T2L>15, T4R–T4L>15, or T8L–T8R>10. Condition G takes place if one of the following occurs: T250L–T250R>15, T500L-T500R>15, T500L–T500R>15, T2L–T2R>15, T4L–T4R>15, or T8R–T8L>15. If just one of the above conditions takes place, the audiogram is categorized as asymmetrical. If none of the conditions occur, the audiogram is instead categorized as symmetrical.

Correlation with Hearing Aid Types

The invention also provides a classification system that correlates audiogram categories with hearing aid types. Certain hearing aid types work well with certain hearing loss types. The classification system essentially recommends a hearing loss type for each possible audiogram category. For example, in one embodiment, audiograms are classified according to the classification scheme shown in FIG. 3 and each combination of configuration, severity, and site of lesion can be linked to a unique hearing aid prescription. In a particular embodiment, only the site of lesion category is used to produce a hearing aid prescription. The hearing aid prescription can be any set of values or recommendations known in the art to recommend certain commercial hearing aids. In one embodiment, if an audiogram is classified as having a sloping configuration, a mild to moderate severity, and a mixed site of lesion, a set of target values for real-ear sound pressure levels for specific input signals can be provided that is unique to that combination of configuration, severity, and site of lesion. Here, the target values constitute the hearing aid prescription. The hearing aid prescription can be satisfied by one or more commercial hearing aids.

In other embodiments, an audiologist generates an audiogram and then classifies the audiogram using a set of rules. Certain values obtained from the classification rules (for example, the average air-conduction thresholds and the average bone-conduction thresholds) are in turn inputted into another formula for determining a hearing aid prescription. Any values obtained from the classification rules can be used in a secondary formula and any hearing aid prescription software program or formula known in the art can be used. For example, one suitable formula is the NAL-NL1 formula, a formula distributed by the National Acoustic Laboratories, located in Chatswood, Australia.

Validation of Rules

The invention also provides methods for developing a set of rules for an audiogram classification system. The method generally includes providing an initial set of rules, validating those rules against expert judges to obtain validation data, and then refining the initial rules using the validation data. The set of rules can be validated by analyzing audiogram classification agreement among judges and between judges and the audiogram classification obtained by the rules. The rules are validated once they classify audiograms similarly to an average judge.

An example of a validation method will now be described. An initial set of rules was developed by Applicant to define the categories shown in FIG. 3 and encoded in a software program. The software categorized a library of 3,686 audiograms using the initial set of rules. Each audiogram included thresholds (including "No Response" indications) present for both ears for air conduction at octave frequencies over the 250-8000 Hz range (with or without interoctave thresholds) and for bone conduction at octave frequencies over the range 250-4000 Hz. The initial rules were used to determine a configuration, severity, and site of lesion for each ear (n=7, 372) and a symmetry category (symmetrical or asymmetrical) for each audiogram. A judge also categorized the audiograms. It immediately became clear that the initial set of rules were not sufficient to categorize the large number of possible audiograms with the desired accuracy. The rules were revised many times until the agreement between the software audiogram classifications and a judge was thought to be satisfactory and an interim set of rules was established.

To validate the interim rules, four additional judges were recruited. Each judge had at least 20 years of experience in clinical audiology. A subset of 231 audiograms (one ear of each) was selected that had approximately equal distribution of the categories shown in FIG. 3. Each judge viewed each audiogram and selected a configuration, severity, and site of lesion. No rules were given to the judges for categorizing the audiograms. They were told to use the definitions that they use in their clinical practices for interpreting audiograms. Only one ear was shown so that their judgments would not be biased by the result of the other ear. Thus, symmetry categories were not selected by the judges.

Based on the results of the five judges, a consensus configuration was determined. The consensus configuration was the configuration category that was chosen by the largest number of judges. There were 19 cases for which there was a tie between two configuration categories. For these cases, the configuration category was judged to be in agreement with the judges if either of the two categories was indicated. The case shown in FIG. 1 (right ear) was eliminated from the analysis because there was no consensus. The initial agreement between the software's selection of the configuration category and the consensus configuration was 68%.

Agreement between pairs of judges and among all the judges are shown in FIG. 8. Results are given as percent of cases on which there was agreement and as a Kappa statistic (in parentheses). The Kappa statistic, introduced by Cohen and described in most statistics texts, is a measure of agreement between categorical data sets that takes into account the probability of agreement due to chance. The Consensus rows shows agreement between each judge and the consensus category for all judges. The All row refers to the rate of agreement across all judges (all judges chose the same category). The Mean of Pairs row is the average agreement between pairs of judges. The Mean Consensus row is the average of the Consensus row. In the case of the seven configuration categories, for example, the likelihood of agreement between a pair of observations due to chance is 1/7. For agreement among all judges, the likelihood of a chance occurrence is $(1/m)^{n-1}$ where m is the number of categories and n is the number of judges.

Agreement between pairs of judges on configuration ranged from 58% to 79% (mean=68%). There was agreement among all five judges for 43% of cases. These somewhat surprisingly low levels of agreement may reflect a) a large proportion of ambiguous audiograms in the sample, such as those in FIGS. 1 & 2, and the lack of standard definitions and common understandings of the configuration categories among expert judges.

The fact that severity categories differed for different configurations complicated the comparison of severity judgments when there was disagreement on configuration. Applicant wished to consider two judgments in agreement when they reflected similar hearing loss magnitudes, even when they were judged to have different configurations. Accordingly, the pairs of severity categories shown in FIG. 9 were considered to be in agreement. Agreement on severity tended to be higher than on configuration. Agreement between pairs of judges ranged from 76 to 87% (mean=83%). There was agreement among all judges for 61% of cases.

Agreement on site of lesion was higher than on configuration but lower than on severity. Agreement between pairs of judges ranged from 61% to 87% (mean=74%). There was agreement among all judges for 50% of cases.

The Consensus rows in FIG. 8 indicate the agreement between each judge and the category chosen by the largest number of judges. For each case, the consensus represents the category with the highest agreement among the panel of judges. It is desirable for the audiogram classification system to have a high agreement with the consensus category.

Agreement between the audiogram classification system and each judge and between the audiogram classification system, the average for all judges, and between the audiogram classification system and consensus categories are shown in FIG. 10. Agreement percent and Kappa values (in parentheses) are shown between categories selected by each judge and by the audiogram classification system. The Consensus column is agreement between the consensus category (selected by the largest number of judges for each case) and the audiogram classification system. These data provide a basis for determining the relative performance of the audiogram classification system and expert judges. For all three audiogram characteristics (configuration, severity, and consensus), the average agreement between the audiogram classification system and the judges was higher than the average interjudge agreement (from FIG. 8, Mean of Pairs) indicating that the audiogram classification system performs better than the average judge.

Figure 11:
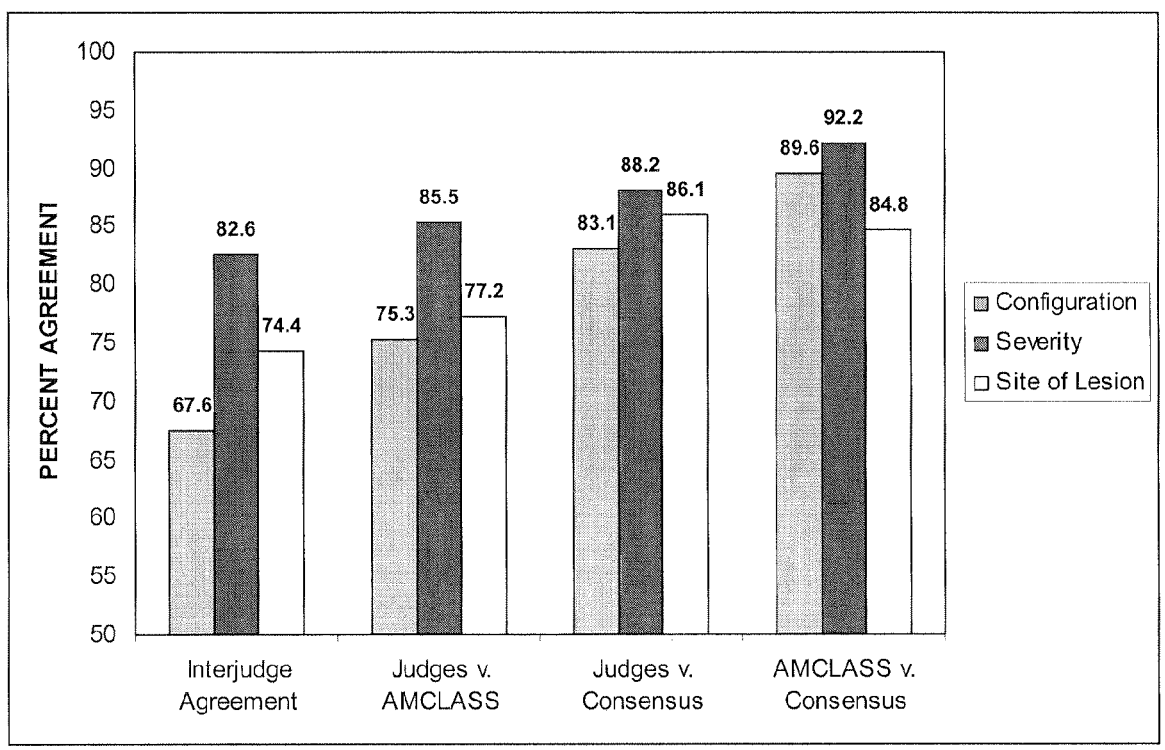
FIG. 11 is a chart showing average comparison data obtained from a validation study of an audiogram classification system.

FIG. 11 summarizes the average comparisons among judges (interjudge agreement), between judges and the audiogram classification system, between judges and the consensus of judges, and between the audiogram classification system and the consensus of judges. For configuration and severity, the best agreement was between the audiogram classification system and the consensus of judges. For site of lesion the audiogram classification system v. consensus was slightly lower than the average agreement between the judges and consensus. Nevertheless, the agreement between the audiogram classification system and consensus for site of lesion was higher than the average interjudge agreement.

Figure 12:
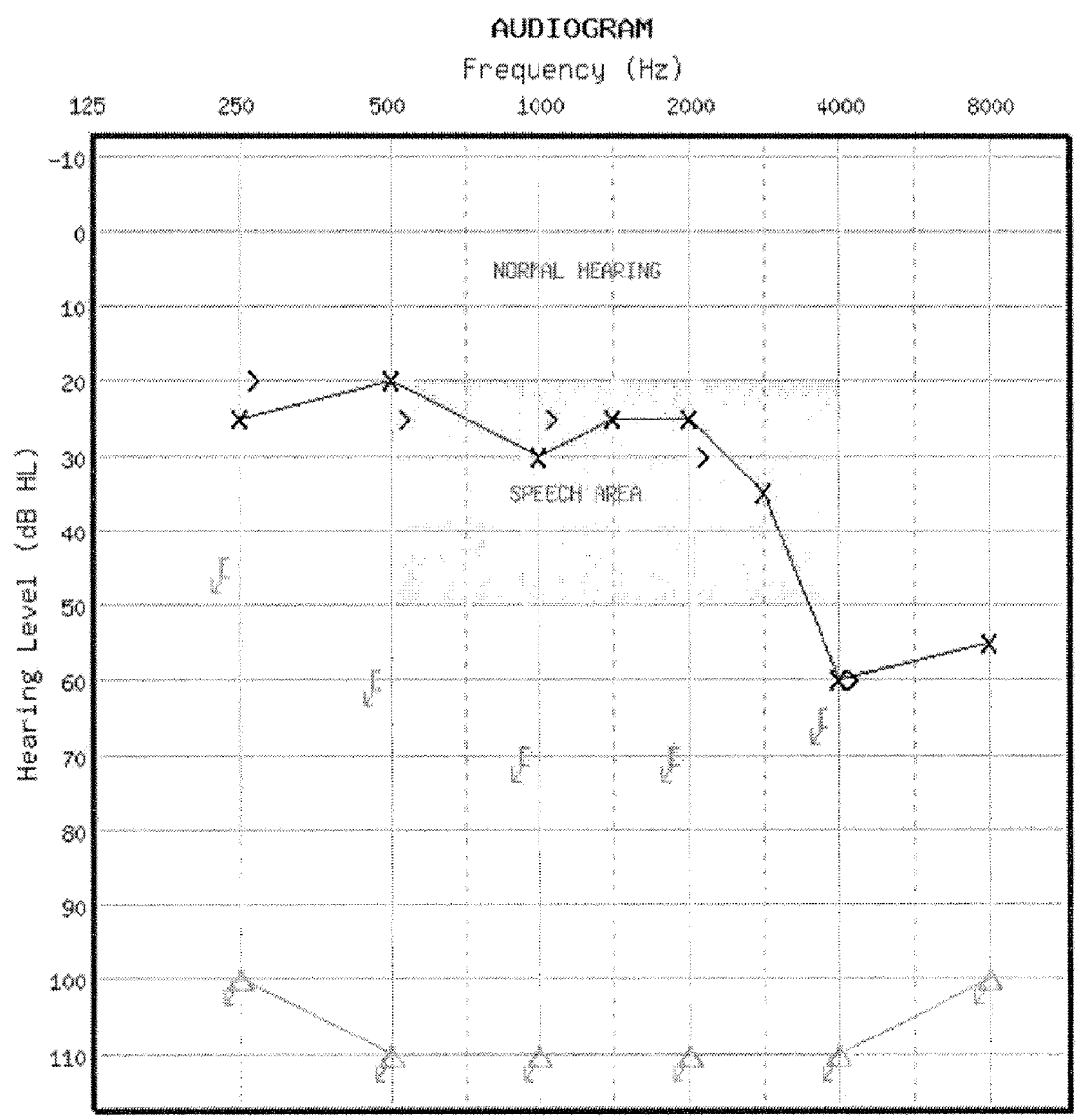
FIG. 12 is an illustration of an audiogram classified as sensorineural or mixed.

The lower agreement between the audiogram classification system and judges for site of lesion compared to configuration and severity results from a lack of common understanding of one of the site of lesion categories. The "sensorineural or mixed" category was intended to be used for audiograms like the one shown for the right ear in FIG. 12. The right ear site of lesion is categorized by the audiogram classification system as sensorineural or mixed. Although many would judge the hearing loss to be sensorineural, a mixed hearing loss cannot be ruled out because of the limitation in bone conduction levels available for testing on clinical audiometers. However, the judges did not consistently use the "sensorineural or mixed" category to describe audiograms of this type. Rather than adjust the rules to maximize agreement between the audiogram classification system and consensus, Applicant felt it is prudent to use that category for cases such as the one shown in FIG. 12. There were 18 cases of this type in the set of audiograms presented to the judges (8%). When these cases are removed from the comparison of the audiogram classification system and consensus, the agreement increases from 85% to 92%.

The validation data just described allowed the design of the rules shown in FIGS. 4-7. These rules maximize agreement with the judges. An analysis of agreement among judges and between judges and the audiogram classification system indicates that the audiogram classification system performs better than the average judge in selecting categories.

An audiogram classification system as described has several applications. One application is to determine the proportion of hearing loss types in a set of audiograms. There is very little information on the prevalence of hearing loss types in the general population or in clinical populations, due at least in part to the lack of standard definitions.

Figure 13:
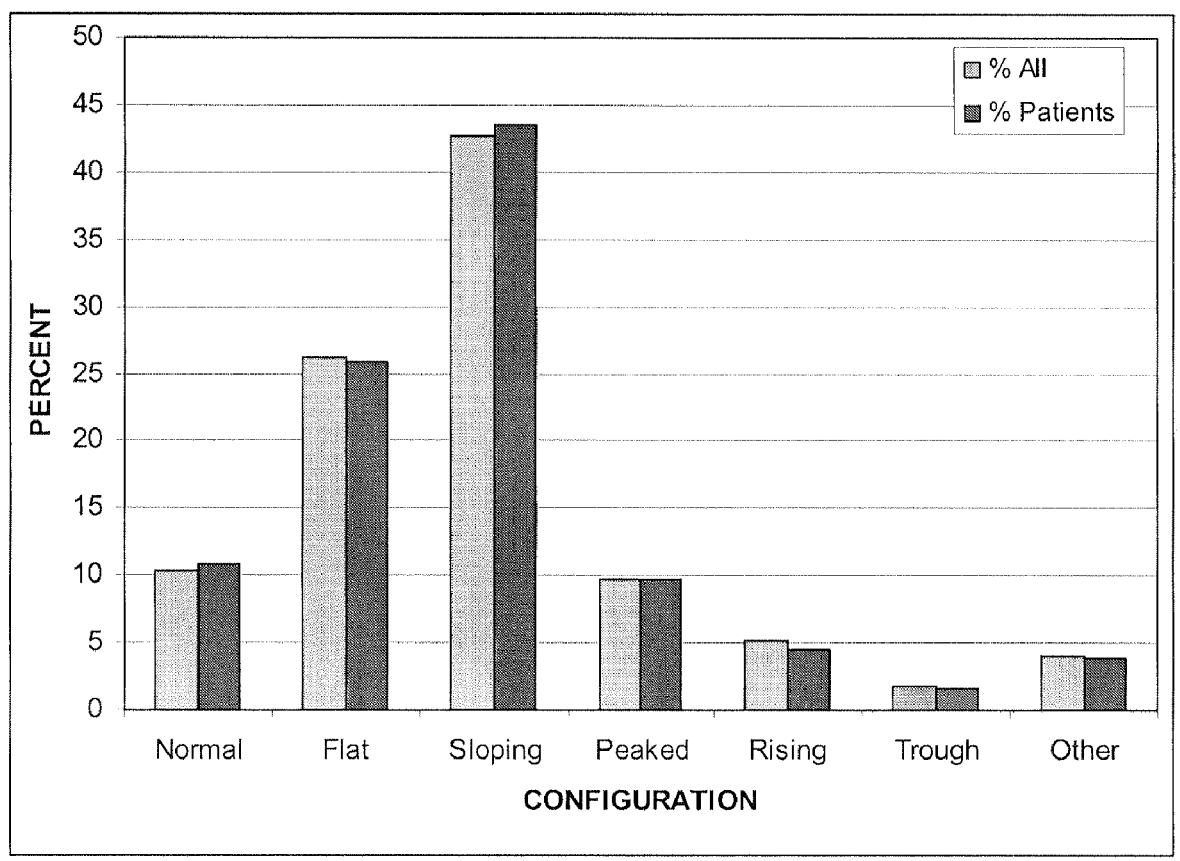
FIG. 13 is a chart showing distribution of configuration types of audiograms categorized during a validation study of an audiogram classification system.
Figure 14:
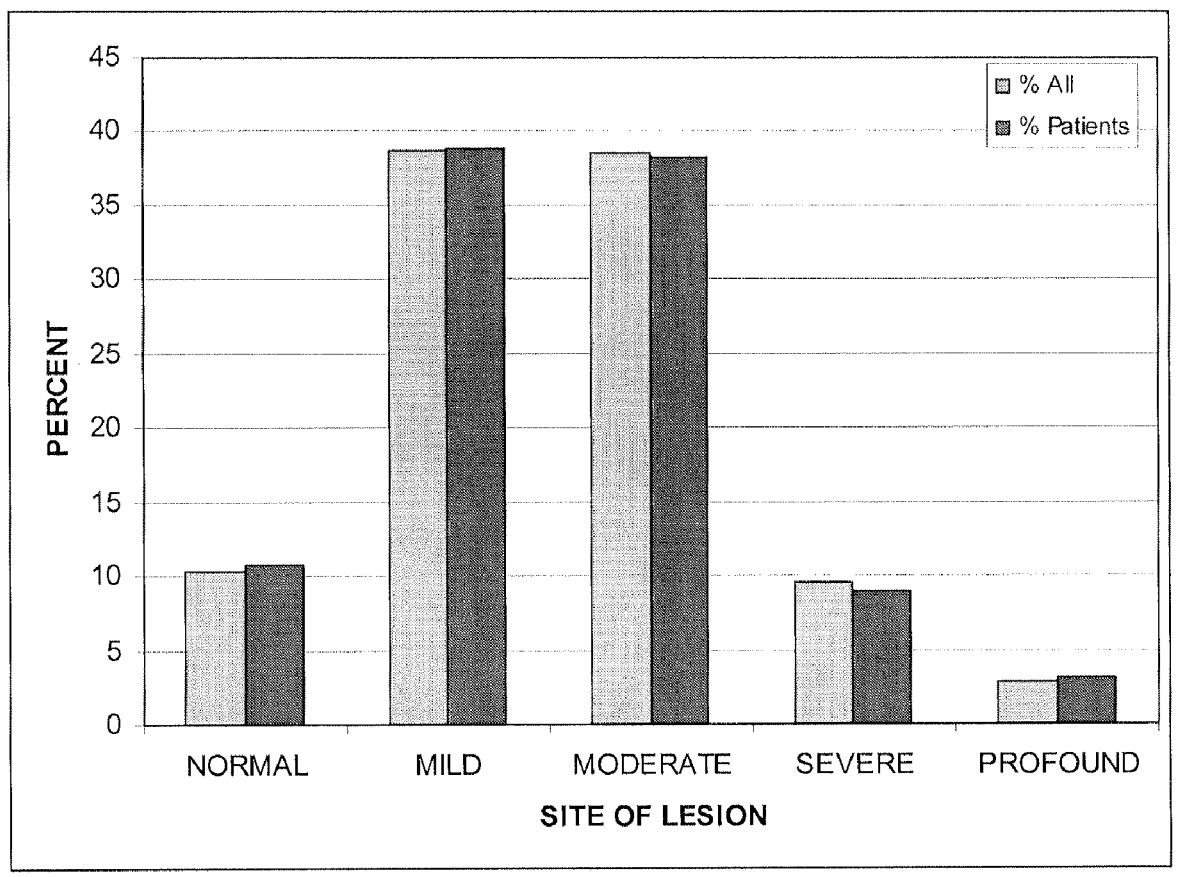
FIG. 14 is a chart showing distribution of severity types of audiograms categorized during a validation study of an audiogram classification system.
Figure 15:
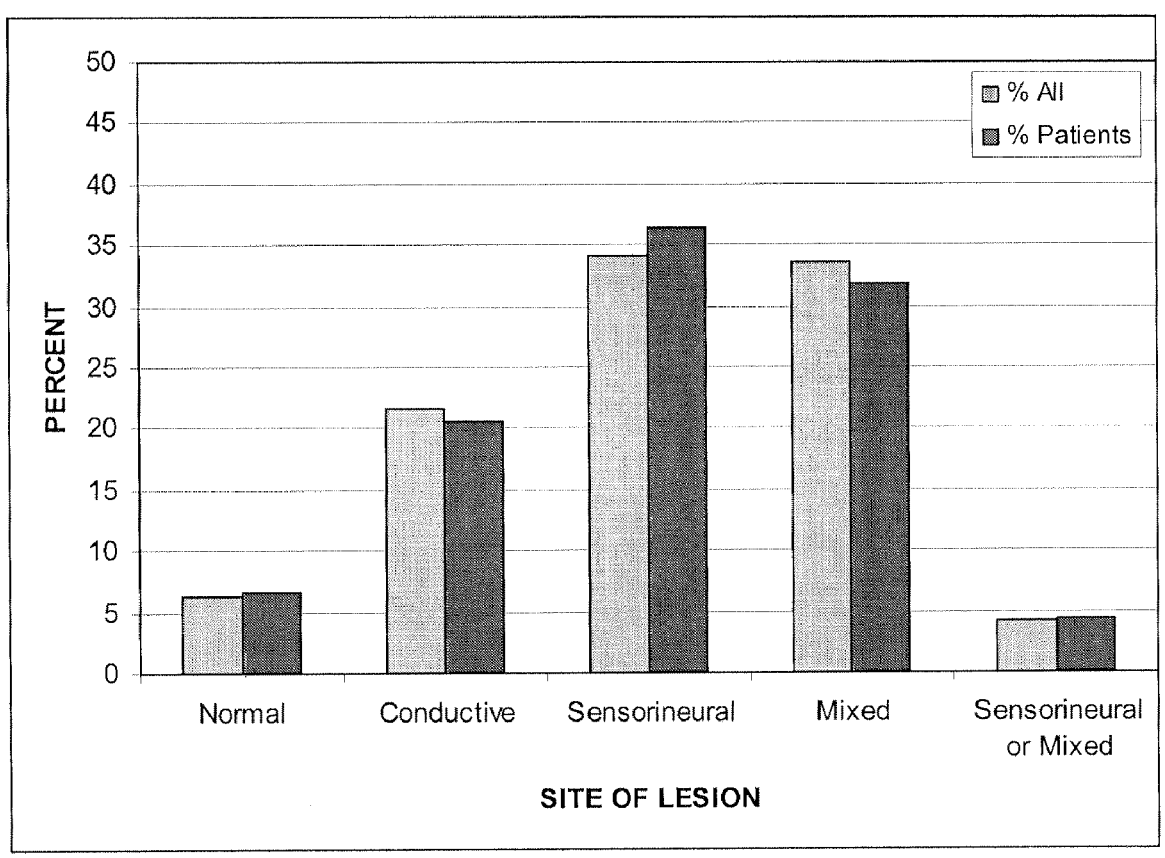
FIG. 15 is a chart showing distribution of site of lesion types of audiograms categorized during a validation study of an audiogram classification system.

Following is an example of the type of analyses that can be done to determine the proportion of hearing loss types in a set of audiograms that have been classified by an audiogram classification system. FIG. 13 shows a distribution of configurations for the database from which the cases used in this validation study were drawn. Distribution of configuration types for audiograms drawn for a hospital-based clinic archive. Percentages are shown for all audiograms (7,372 ears) and for patients with repeated tests omitted (6,292 ears). FIG. 14 shows the distribution of severities for the database with all audiograms included and with repeat tests excluded.

For combination categories (e.g. mild-moderate) the following rules were used to group them into the five major categories. When the combination consisted of adjacent categories (e.g. mild-moderate) it was grouped with the less severe category, with the following exceptions. Normal-mild and mild-normal were grouped with mild. When the combination spanned three major categories it was grouped with the category in the middle (e.g. severe-mild was grouped with moderate). Combination severities such as mild-moderate sloping hearing loss and moderate-mild rising hearing loss were grouped with one of the major categories according to the rules described in the figure legend. FIG. 7 shows the distribution of site of lesion for the database with all audiograms included and with repeat tests excluded.

While a preferred embodiment of the present invention has been described, it should be understood that various changes, adaptations and modifications may be made therein without departing from the spirit of the invention and the scope of the appended claims.

What is claimed is:

1. A method for automatically classifying an audiogram with a processor programmed with a non-transitory software program to perform the method, the method comprising:
    selecting a configuration for the audiogram with the non-transitory software program, the configuration selected from the group consisting of a normal configuration, a flat configuration, a sloping configuration, a rising configuration, a trough configuration, a peaked configuration, and an other configuration;
    selecting a severity for the audiogram with the non-transitory software program, the severity depending on the selected configuration, wherein no severity is selected for the normal configuration, wherein the severity for the flat configuration is selected from the group consisting of mild, moderate, severe, and profound, wherein the severity for the sloping configuration is selected from the group consisting of normal-mild, normal-moderate, normal-severe, mild-moderate, mild-severe, moderate-severe, and severe-profound, wherein the severity for the rising configuration is selected from the group consisting of mild-normal, moderate-normal, moderate-mild, severe-normal, severe-mild, severe-moderate, profound-severe, and profound, wherein the severity for the trough configuration is selected from the group consisting of mild, moderate and severe, wherein the severity for the peaked configuration is selected from the group consisting of mild, moderate and severe, wherein the severity for the other configuration is selected from the group consisting of mild, moderate and severe;
    selecting a site of lesion for the audiogram with the non-transitory software program, the site of lesion selected from the group consisting of a conductive site of lesion, a sensorineural site of lesion, a mixed site of lesion, and a mixed/sensorineural site of lesion; and
    selecting a symmetry for the audiogram with the non-transitory software program, the symmetry selected from the group consisting of a symmetrical symmetry and an asymmetrical symmetry.

2. The method of claim 1 wherein the selecting is performed using a set of rules.

3. The method of claim 2 wherein said set of rules ignore local irregularities on an audiogram.

4. The method of claim 2 wherein said set of rules are rules that have been validated to maximize agreement between judges.

5. The method of claim 1 further comprising generating a hearing aid prescription with the non-transitory software program, wherein the hearing aid prescription is based on a selected configuration, severity, and/or site of lesion.

6. The method of claim 2 further comprising using one or more values obtained from said set of rules in a hearing aid prescription formula, the hearing aid prescription formula being configured to generate a hearing aid prescription.

7. The method of claim 6 wherein said one or more values includes air-conduction threshold averages and bone-conduction threshold averages.

8. The method of claim 1, wherein the processor is part of an audiometer.

9. The method of claim 1, wherein the processor is part of a computer.

10. A method for automatically classifying an audiogram with a processor programmed with a non-transitory software program to perform the method, the method comprising:
    selecting a configuration for the audiogram with the non-transitory software program, the configuration selected from the group consisting of a normal configuration, a flat configuration, a sloping configuration, a rising configuration, a trough configuration, a peaked configuration, and an other configuration; and
    selecting a severity for the audiogram with the non-transitory software program, the severity depending on the selected configuration, wherein no severity is selected for the normal configuration, wherein the severity for the flat configuration is selected from the group consisting of mild, moderate, severe, and profound, wherein the severity for the sloping configuration is selected from the group consisting of normal-mild, normal-moderate, normal-severe, mild-moderate, mild-severe, moderate-severe, and severe-profound, wherein the severity for the rising configuration is selected from the group consisting of mild-normal, moderate-normal, moderate-mild, severe-normal, severe-mild, severe-moderate, profound-severe, and profound, wherein the severity for the trough configuration is selected from the group consisting of mild, moderate and severe, wherein the severity for the peaked configuration is selected from the group consisting of mild, moderate and severe, wherein the severity for the other configuration is selected from the group consisting of mild, moderate and severe, wherein the configuration and the severity are selected using rules based on at least one variable selected from the group consisting of a threshold average, moving threshold averages, mean of moving threshold averages, a maximum threshold, a minimum threshold, a maximum moving threshold average, and a minimum moving threshold average.

11. The method of claim 10 further comprising selecting said normal configuration using rules based on said threshold average, said moving threshold averages, and said maximum moving threshold average.

12. The method of claim 10 further comprising selecting said flat configuration using rules based on said moving threshold averages, said maximum threshold, said minimum threshold, said maximum moving threshold average, and said minimum moving threshold average.

13. The method of claim 12 further comprising selecting a severity for said flat configuration with the non-transitory software program, using rules based on said threshold average.

14. The method of claim 10 further comprising selecting said sloping configuration using rules based on said moving threshold averages, said maximum moving threshold average, and said minimum moving threshold average.

15. The method of claim 14 further comprising selecting a severity for said sloping configuration with the non-transitory software program, using rules based on moving threshold averages for a first frequency region and a second frequency region, wherein the second frequency region is higher than the first frequency region.

16. The method of claim 10 further comprising selecting said rising configuration using rules based on said moving threshold averages, said maximum moving threshold average, and said minimum moving threshold average.

17. The method of claim 16 further comprising selecting a severity for said rising configuration with the non-transitory software program using rules based on moving threshold averages for a first frequency region and a second frequency region, wherein the second frequency region is higher than the first frequency region.

18. The method of claim 10 further comprising selecting said trough configuration using rules based on said moving threshold averages and said maximum moving threshold average.

19. The method of claim 18 further comprising selecting a severity for said trough configuration with the non-transitory software program using rules based on said maximum moving threshold average.

20. The method of claim 10 further comprising selecting said peaked configuration using rules based on said moving threshold averages and said maximum moving threshold average.

21. The method of claim 20 further comprising selecting a severity for said peaked configuration with the non-transitory software program using rules based on said threshold average.

22. The method of claim 10 further comprising selecting said other configuration when rules for said normal configuration, said flat configuration, said sloping configuration, said rising configuration, said trough configuration, and said peaked configuration are not satisfied.

23. The method of claim 22 further comprising selecting a severity for said other configuration with the non-transitory software program using rules based on said threshold average.

24. The method of claim 10 further comprising generating a hearing aid prescription with the non-transitory software program, wherein the hearing aid prescription is based on a selected configuration, severity, and/or site of lesion.

25. The method of claim 10 further comprising using one or more variables obtained from said rules in a hearing aid prescription formula, the hearing aid prescription formula being configured to generate a hearing aid prescription.

26. A method for automatically classifying an audiogram with a processor programmed with a non-transitory software program to perform the method, the method comprising selecting a configuration for the audiogram with the processor using rules that incorporate variables, said variables including a threshold average, moving threshold averages, a mean of moving threshold averages, a maximum threshold, a minimum threshold, a maximum moving threshold average, and a minimum moving threshold average.

27. The method of claim 26 wherein the selecting a configuration includes selecting a configuration from the group consisting of a normal configuration, a flat configuration, a sloping configuration, a rising configuration, a trough configuration, a peaked configuration, and an other configuration.

28. The method of claim 27 further comprising selecting a severity with the non-transitory software program, the severity depending on the selected configuration, wherein no severity is selected for the normal configuration, wherein the severity for the flat configuration is selected from the group consisting of mild, moderate, severe, and profound, wherein the severity for the sloping configuration is selected from the group consisting of normal-mild, normal-moderate, normal-severe, mild-moderate, mild-severe, moderate-severe, and severe-profound, wherein the severity for the rising configuration is selected from the group consisting of mild-normal, moderate-normal, moderate-mild, severe-normal, severe-mild, severe-moderate, profound-severe, and profound, wherein the severity for the trough configuration is selected from the group consisting of mild, moderate and severe, wherein the severity for the peaked configuration is selected from the group consisting of mild, moderate and severe, wherein the severity for the other configuration is selected from the group consisting of mild, moderate and severe.

29. The method of claim 26 further comprising selecting a site of lesion with the non-transitory software program, wherein the site of lesion selected from the group consisting of a conductive site of lesion, a sensorineural site of lesion, a mixed site of lesion, and a sensorineural/mixed site of lesion.

30. The method of claim 26 further comprising selecting a symmetry with the non-transitory software program, wherein the symmetry is selected from the group consisting of symmetrical and asymmetrical.

31. A non-transitory computer-readable storage medium with an executable software program stored thereon, the software program being executable by a processor to perform a method for automatically classifying an audiogram, the method comprising
  selecting a configuration for the audiogram, the configuration selected from the group consisting of a normal configuration, a flat configuration, a sloping configuration, a rising configuration, a trough configuration, a peaked configuration, and an other configuration,
  selecting a severity for the audiogram, the severity depending on the selected configuration, wherein no severity is selected for the normal configuration, wherein the severity for the flat configuration is selected from the group consisting of mild, moderate, severe, and profound, wherein the severity for the sloping configuration is selected from the group consisting of normal-mild, normal-moderate, normal-severe, mild-moderate, mild-severe, moderate-severe, and severe-profound, wherein the severity for the rising configuration is selected from the group consisting of mild-normal, moderate-normal, moderate-mild, severe-normal, severe-mild, severe-moderate, profound-severe, and profound, wherein the severity for the trough configuration is selected from the group consisting of mild, moderate and severe, wherein the severity for the peaked configuration is selected from the group consisting of mild, moderate and severe, wherein the severity for the other configuration is selected from the group consisting of mild, moderate and severe,
  selecting a site of lesion for the audiogram, the site of lesion selected from the group consisting of a conductive site of lesion, a sensorineural site of lesion, a mixed site of lesion, and a mixed/sensorineural site of lesion, and
  selecting a symmetry for the audiogram, the symmetry selected from the group consisting of a symmetrical symmetry and an asymmetrical symmetry.

32. A non-transitory computer-readable storage medium with an executable software program stored thereon, the software program being executable by a processor to perform a method for automatically classifying an audiogram, the method comprising selecting a configuration for the audiogram, the configuration selected from the group consisting of a normal configuration, a flat configuration, a sloping configuration, a rising configuration, a trough configuration, a peaked configuration, and an other configuration and selecting a severity for the audiogram, the severity depending on the selected configuration, wherein no severity is selected for the normal configuration, wherein the severity for the flat configuration is selected from the group consisting of mild, moderate, severe, and profound, wherein the severity for the sloping configuration is selected from the group consisting of normal-mild, normal-moderate, normal-severe, mild-moderate, mild-severe, moderate-severe, and severe-profound, wherein the severity for the rising configuration is selected from the group consisting of mild-normal, moderate-normal, moderate-mild, severe-normal, severe-mild, severe-moderate, profound-severe, and profound, wherein the severity for the trough configuration is selected from the group consisting of mild, moderate and severe, wherein the severity for the peaked configuration is selected from the group consisting of mild, moderate and severe, wherein the severity for the other configuration is selected from the group consisting of mild, moderate and severe, wherein the configuration and the severity are selected using rules based on at least one variable selected from the group consisting of a threshold average, moving threshold averages, mean of moving threshold averages, a maximum threshold, a minimum threshold, a maximum moving threshold average, and a minimum moving threshold average.

33. A non-transitory computer-readable storage medium with an executable software program stored thereon, the software program being executable by a processor to perform a method for automatically classifying an audiogram, the method comprising selecting a configuration for the audiogram using rules that incorporate variables, said variables including a threshold average, moving threshold averages, a mean of moving threshold averages, a maximum threshold, a minimum threshold, a maximum moving threshold average, and a minimum moving threshold average.

34. The non-transitory computer-readable storage medium of claim 31, wherein the processor is part of a computer.

35. An audiometer comprising a processor and the non-transitory computer-readable storage medium as in claim 31.

* * * * *